United States Patent
Kuo

(10) Patent No.: US 9,381,375 B2
(45) Date of Patent: Jul. 5, 2016

(54) METHOD FOR KILLING AND TRACING BACTERIA BY COATING SAME WITH SELF-ASSEMBLED GOLD NANOSHELL LAYER AND PRODUCING PHOTOTHERMAL DECOMPOSITION AND COLD LIGHT BY MEANS OF LASER

(71) Applicant: Wen-Shuo Kuo, Tainan (TW)

(72) Inventor: Wen-Shuo Kuo, Tainan (TW)

( * ) Notice: Subject to any disclaimer, the term of this patent is extended or adjusted under 35 U.S.C. 154(b) by 0 days.

(21) Appl. No.: 14/851,060

(22) Filed: Sep. 11, 2015

(65) Prior Publication Data

US 2016/0059033 A1    Mar. 3, 2016

Related U.S. Application Data

(63) Continuation of application No. PCT/CN2013/073450, filed on Mar. 29, 2013.

(51) Int. Cl.
*A61L 2/04* (2006.01)
*A61N 5/06* (2006.01)
*A61N 5/067* (2006.01)

(52) U.S. Cl.
CPC . *A61N 5/062* (2013.01); *A61L 2/04* (2013.01); *A61N 5/0624* (2013.01); *A61N 2005/067* (2013.01)

(58) Field of Classification Search
CPC ..... A61L 2/04; A61N 5/062; A61N 2005/067
USPC ............................................. 604/20; 422/22
See application file for complete search history.

(56) References Cited

U.S. PATENT DOCUMENTS

2004/0253138 A1    12/2004    Malak
2012/0143043 A1     6/2012    Peyman

FOREIGN PATENT DOCUMENTS

CN          102000397 A    4/2011

OTHER PUBLICATIONS

Shu, Weiguo et al., Research advance of metal nanoparticles prepared by microorganism, Journal of Functional Materials, 2007 supplement, vol. 38, 2052-2055.
Zhang, Lisha et al., Research progress in gold nanostructures with photothermal effects, Materials Review, vol. 26, No. 10, 5-9.

*Primary Examiner* — Sean E Conley
(74) *Attorney, Agent, or Firm* — Alan D. Kamrath; Kamrath IP Lawfirm, P.A.

(57) ABSTRACT

As an extremely simple and efficiency way to kill Gram-positive, -negative, -multidrug resistant bacteria, and in particular methicillin-resistant *Staphylococcus aureus*, gold nanoparticles were grown self-assembling to yield gold nanoshells on the surface of bacteria (bacteria coated with gold nanoshells or bacterial nanomaterials) by the solution contained gold ion but no adding reductant. The bacteria with gold nanoshells still kept their vitality and mobility for weeks. Due to gold with the high efficiently to convert absorbed radiation into heat for serving as photothermal therapeutic agents, enabled the bacteria coated with gold nanoshells acted as photothermal agents to kill bacteria efficiently. As a result, these bacterial nanomaterials showed impressive photothermolytic efficacy to reduce the viability of bacteria with laser irradiation and an excellent ability to emit photoluminescence after laser irradiation which was generated from the dead bacteria coated with bacterial nanomaterials. The stronger photoluminescence was emitted, the more bacteria were killed. Moreover, the photoluminescence which was able to sustain femtosecond laser exposure, keep luminescence emitted and prevent from photobleaching was still generated after being exposed for hours. It is very eligible to act as optical contrast agents. As a result, these nanomaterials were definitely able to serve as brand-new contrast agents or indicators to determine viability, track and localize bacteria in clinical applications.

9 Claims, 44 Drawing Sheets

Bacteria

Solution contained gold ion ⟶

Bacteria coated with gold nanoshells

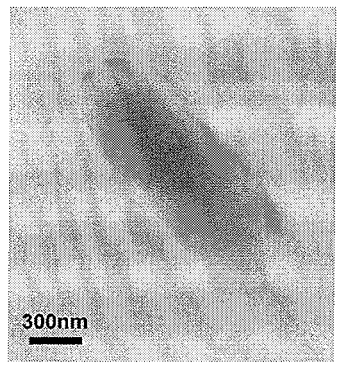
Figure 3-a
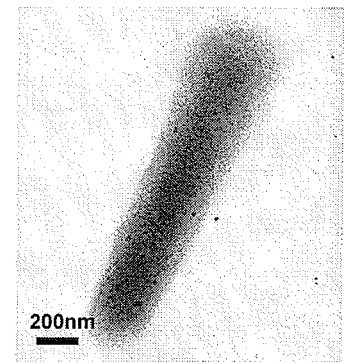
Figure 3-b
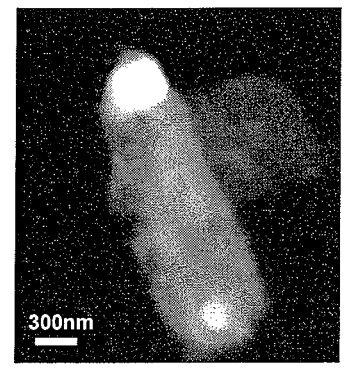
Figure 3-c
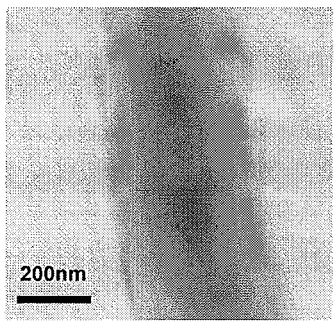
Figure 3-d
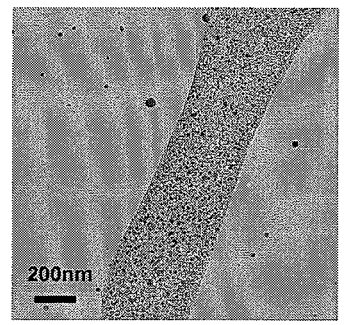
Figure 3-e
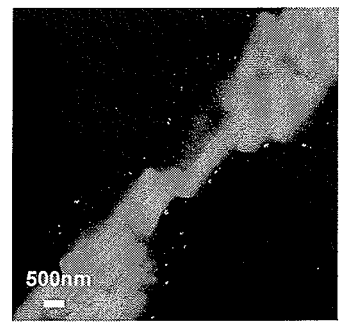
Figure 3-f
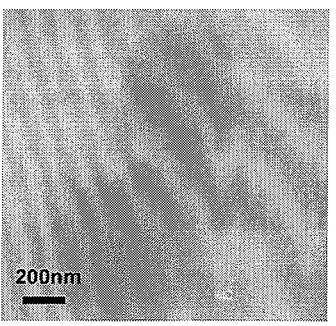
Figure 3-g
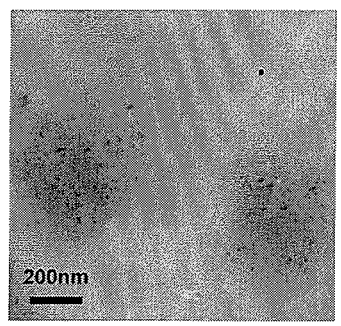
Figure 3-h
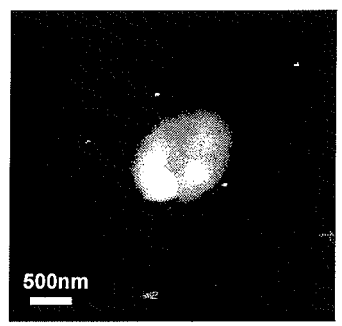
Figure 3-i

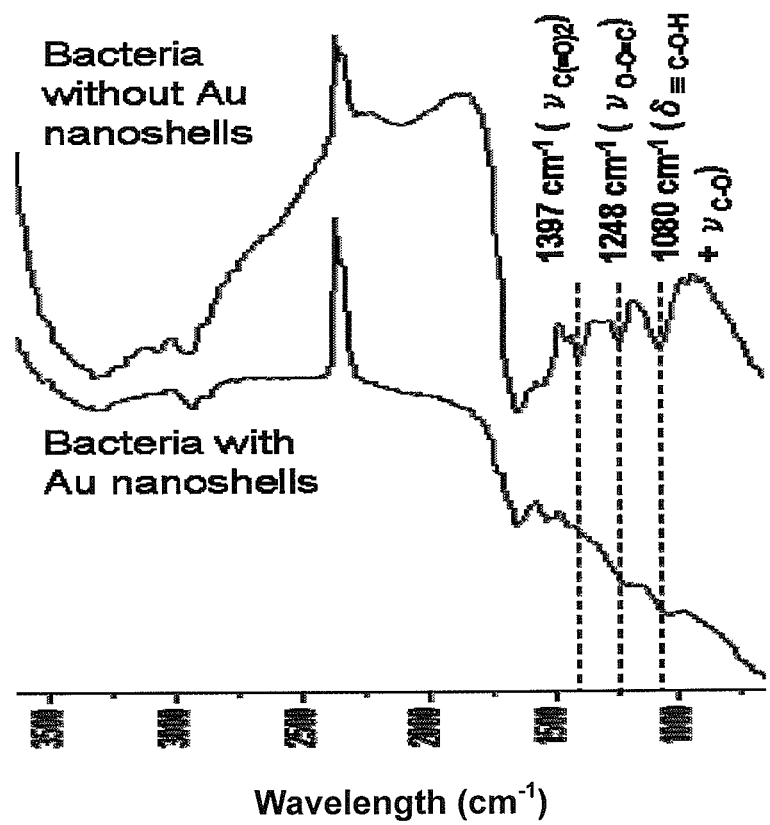
Figure 4-a

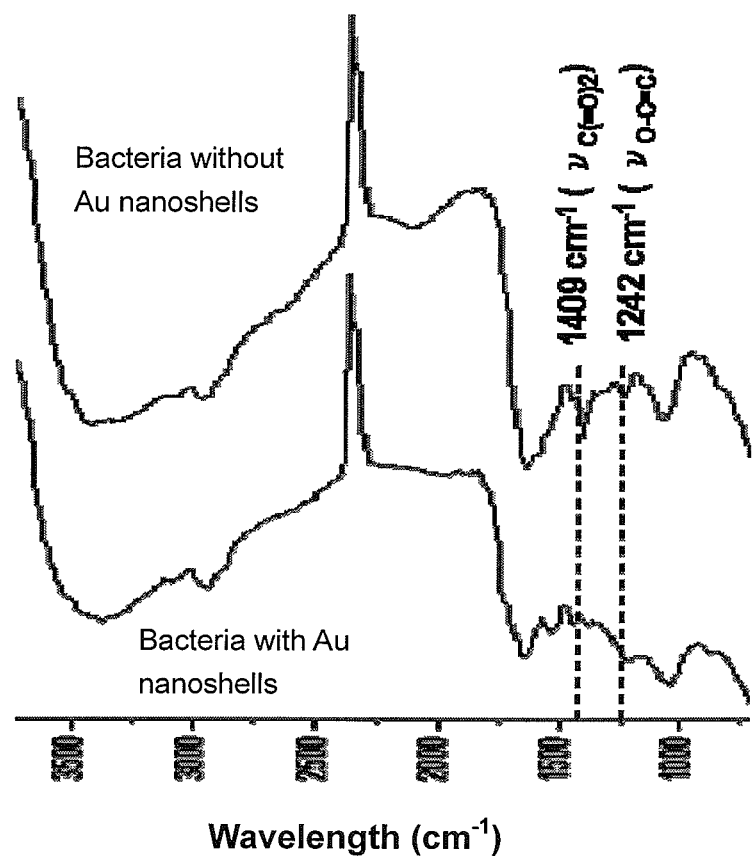
Figure 4-b

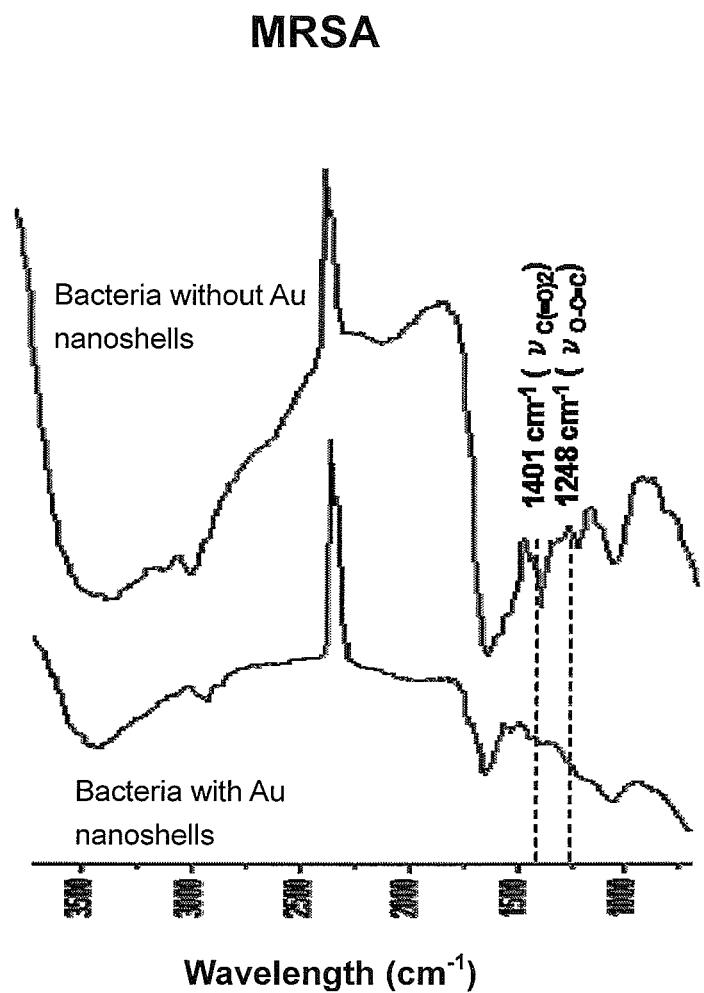
Figure 4-c

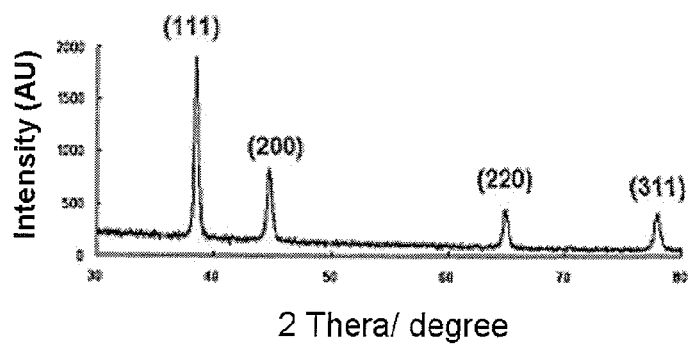
Figure 5-a1

BL21 of *Escherichia coli*
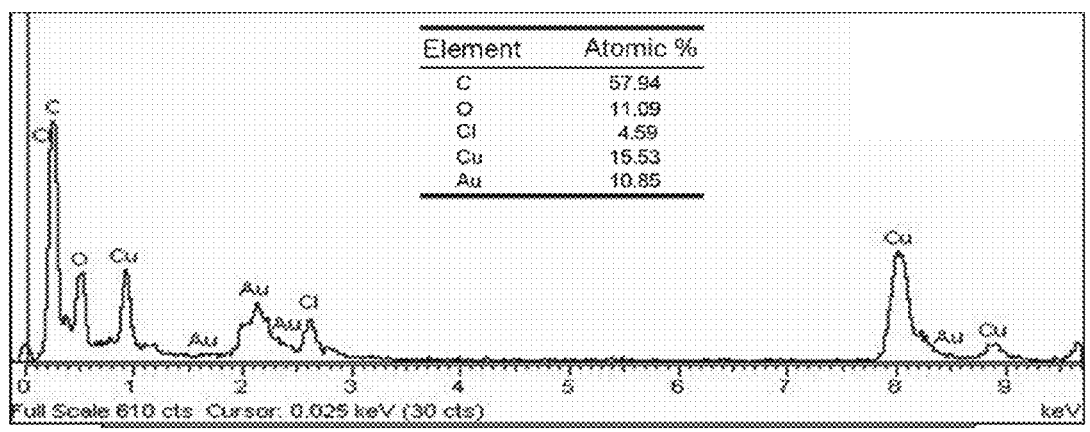
Figure 5-a2

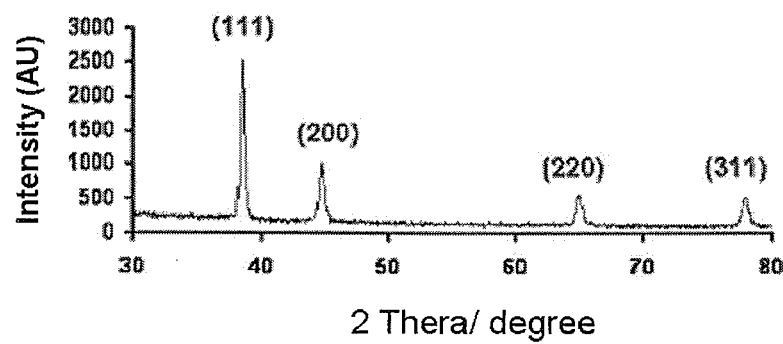
Figure 5-b1

*Bacillus subtilis*
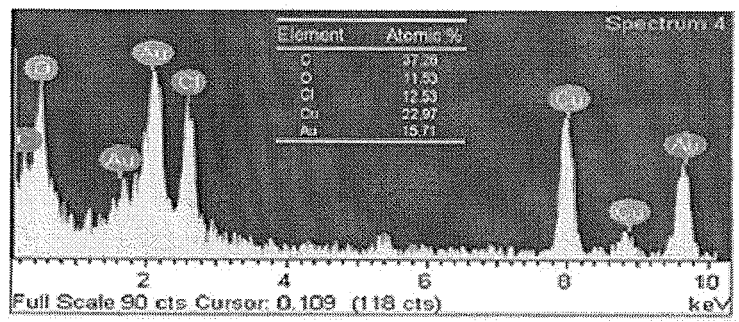
Figure 5-b2

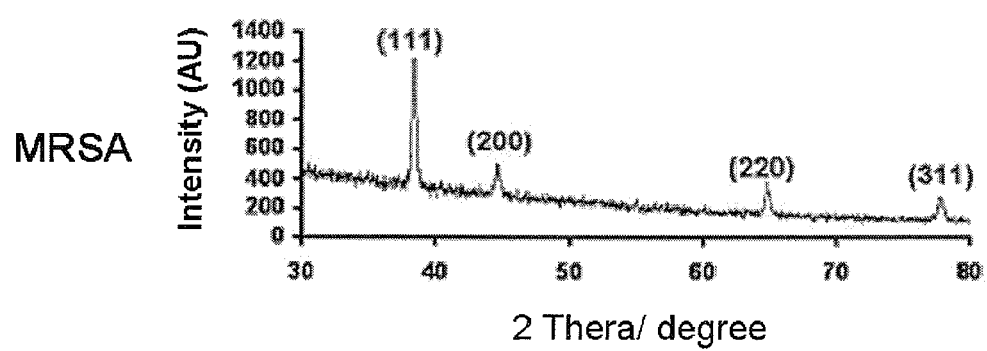
Figure 5-c1

MRSA 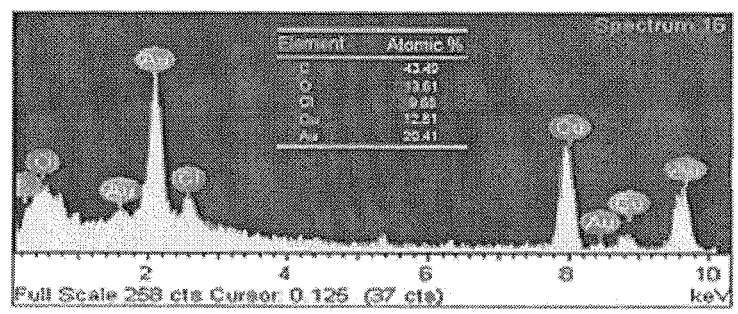
Figure 5-c2

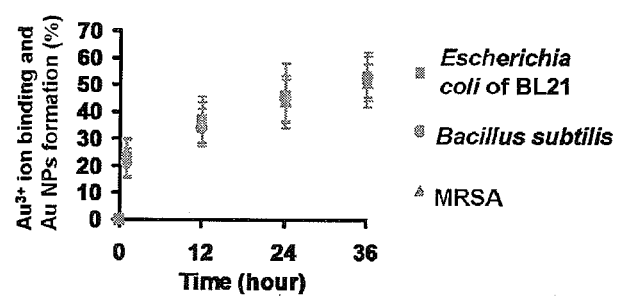
Figure 6-a
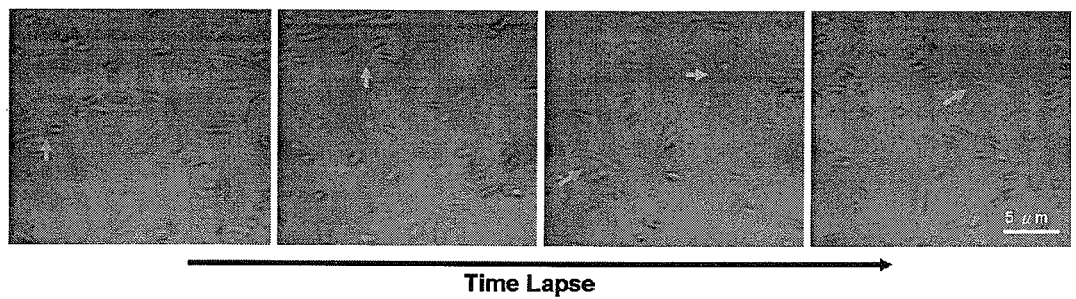
Figure 6-b
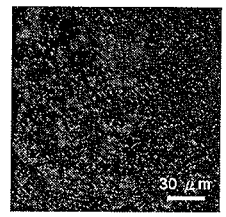
Figure 6-c

*Escherichia coli* of BL21 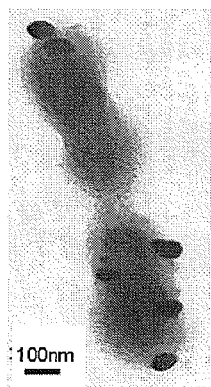     *Bacillus subtilis* 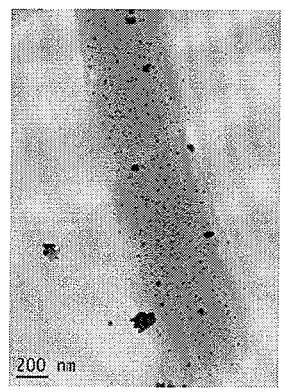     MRSA 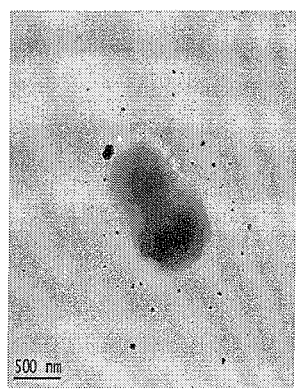
Figure 6-d     Figure 6-e     Figure 6-f BL21 of
Escherichia coli
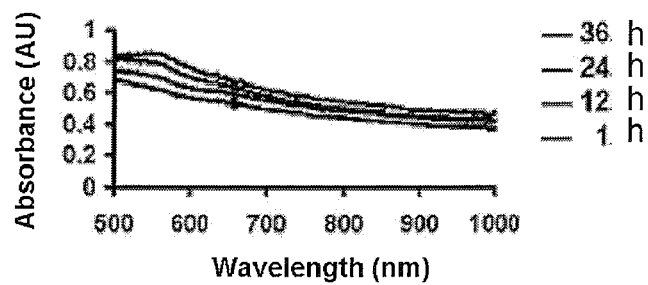
Figure 7-a
Bacillus
subtilis
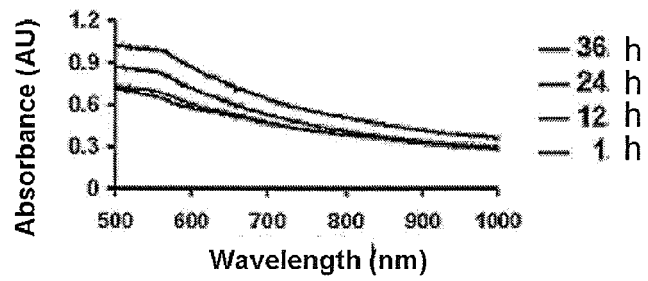
Figure 7-b
MRSA
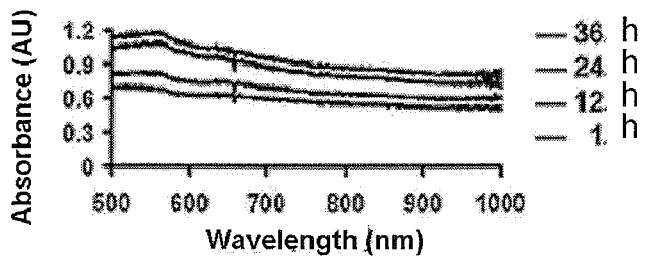
Figure 7-c

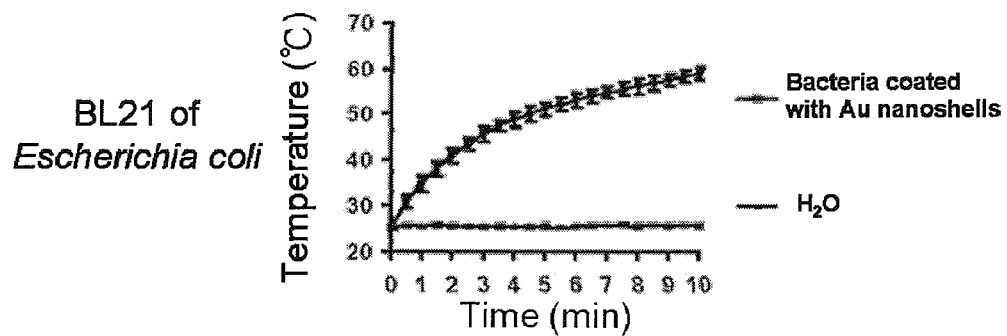
Figure 8-a
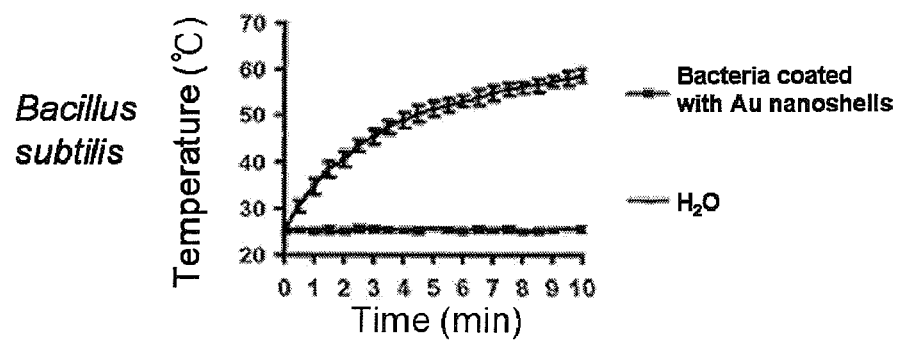
Figure 8-b
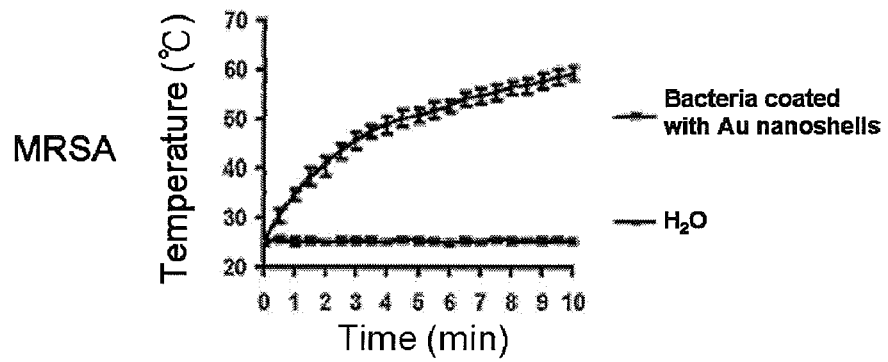
Figure 8-c

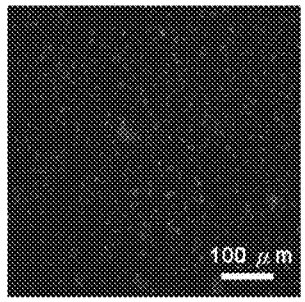
**BL21 of *Escherichia coli***
Bacteria coated with Au nanoshells with no laser exposure
Figure 10-a1
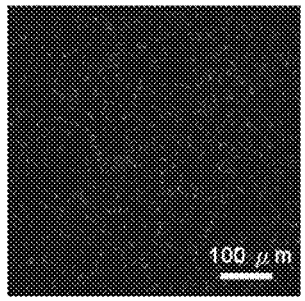
*Bacillus subtilis*
Bacteria coated with Au nanoshells with no laser exposure
Figure 10-a2
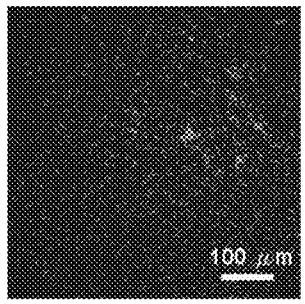
**BL21 of *Escherichia coli***
Bacteria coated with Au nanoshells exposed to CW-NIR laser
Figure 10-b1
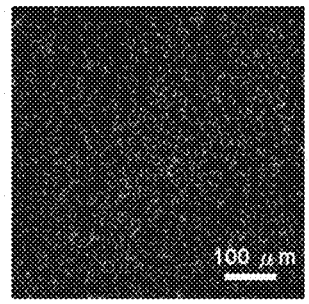
*Bacillus subtilis*
Bacteria coated with Au nanoshells exposed to CW-NIR laser
Figure 10-b2

BL21 of *Escherichia coli*
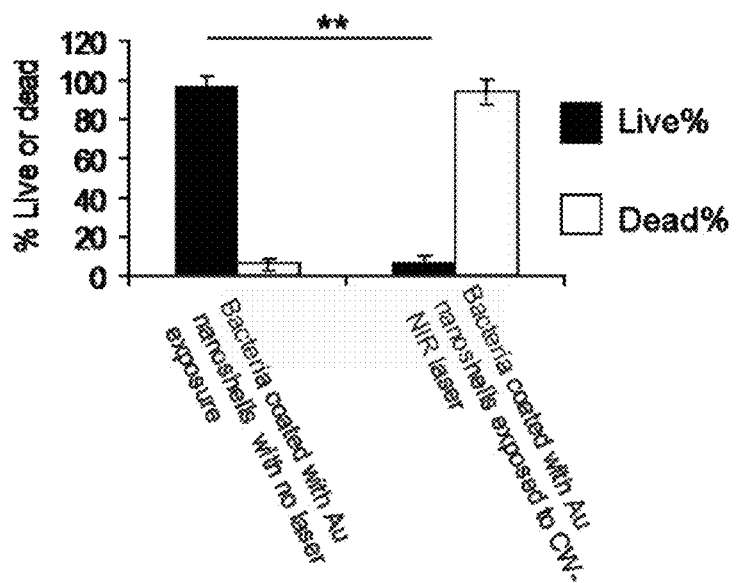
Figure 10-c1
*Bacillus subtilis*
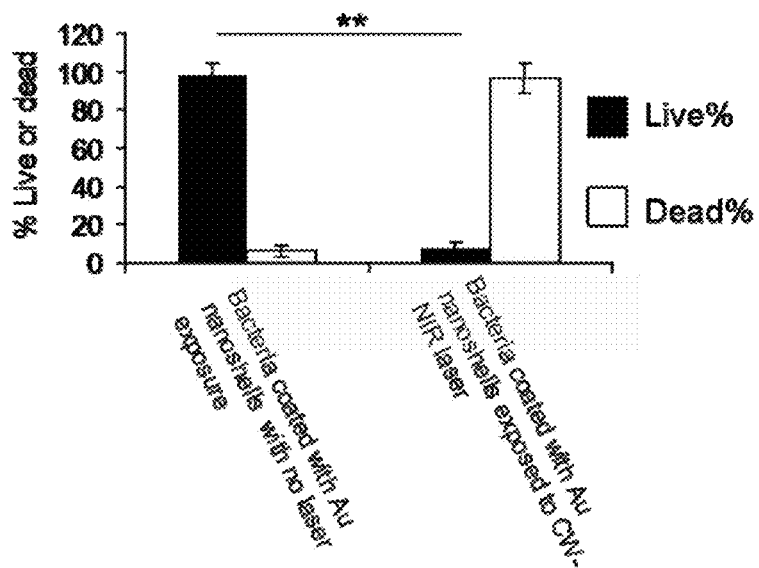
Figure 10-c2

BL21 of *Escherichia coli*
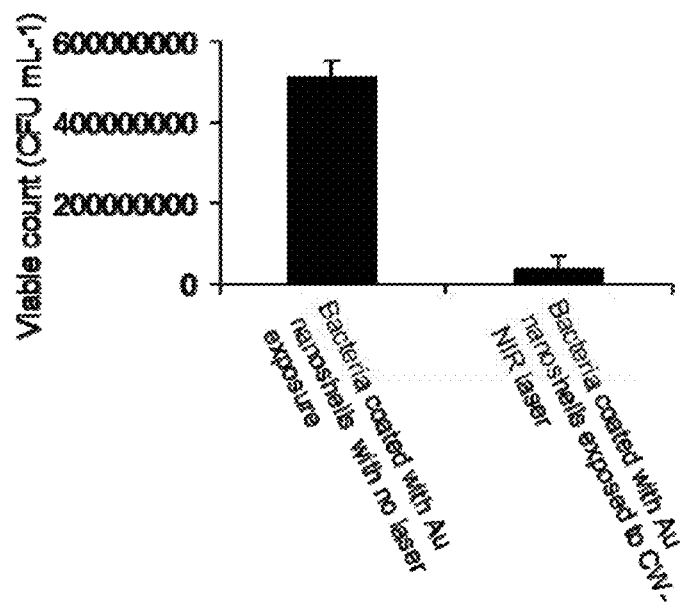
Figure 10-d1
*Bacillus subtilis*
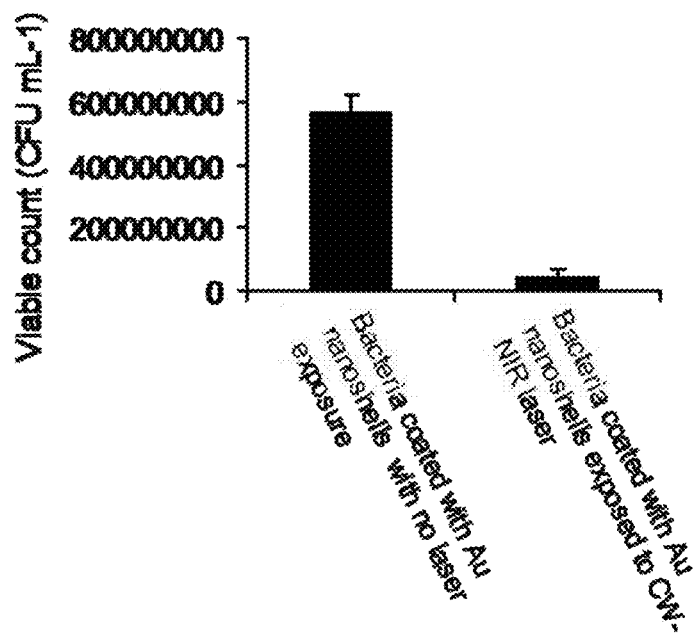
Figure 10-d2

**BL21 of *Escherichia coli***

Bacteria coated with Au nanoshells exposed to femtosecond laser

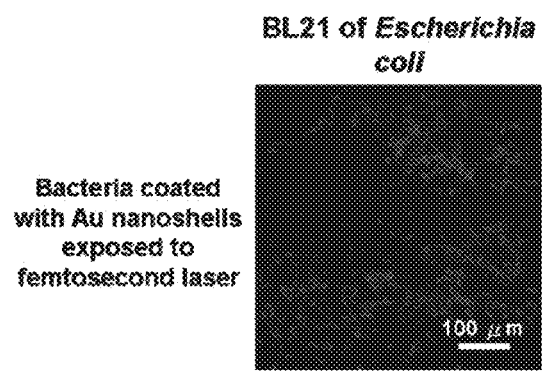

Figure 10-e1

*Bacillus subtilis*

Bacteria coated with Au nanoshells exposed to femtosecond laser

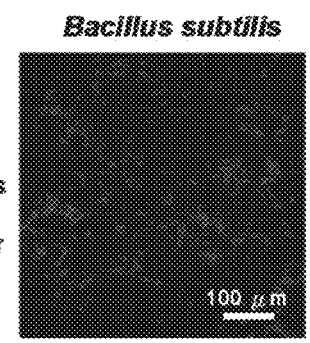

Figure 10-e2

**BL21 of *Escherichia coli***

Bacteria coated with Au nanoshells exposed to femtosecond laser

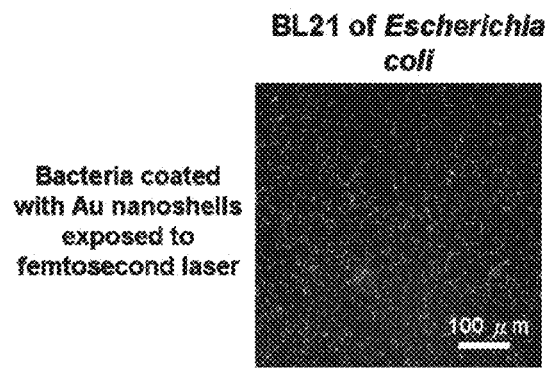

Figure 10-f1

*Bacillus subtilis*

Bacteria coated with Au nanoshells exposed to femtosecond laser

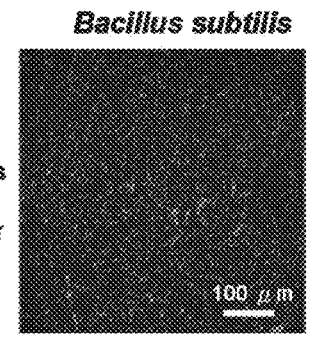

Figure 10-f2

BL21 of *Escherichia coli*
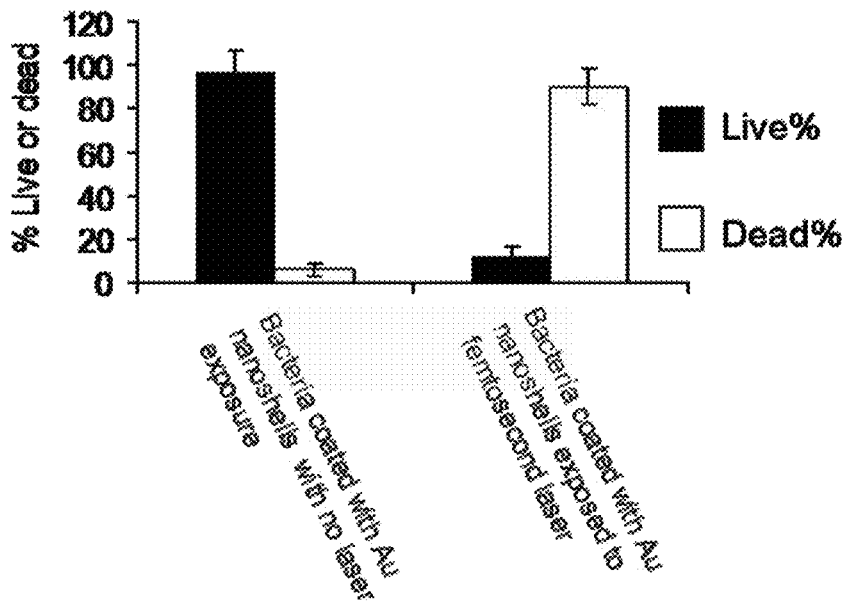
Figure 10-g1
*Bacillus subtilis*
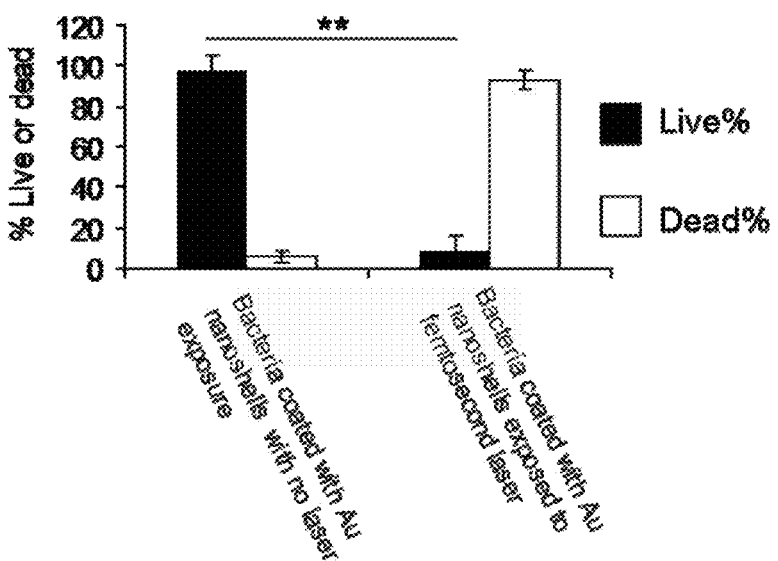
Figure 10-g2

**BL21 of *Escherichia coli***

After autoclave, bacteria coated with Au nanoshells exposed to femtosecond laser

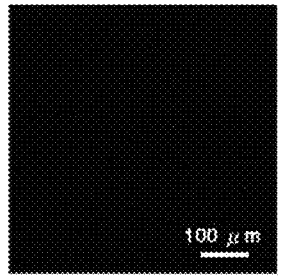

Figure 10-h1

*Bacillus subtilis*

After autoclave, bacteria coated with Au nanoshells exposed to femtosecond laser

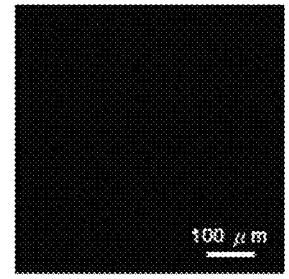

Figure 10-h2

**BL21 of *Escherichia coli***

After antibiotic treatment, bacteria coated with Au nanoshells exposed to femtosecond laser

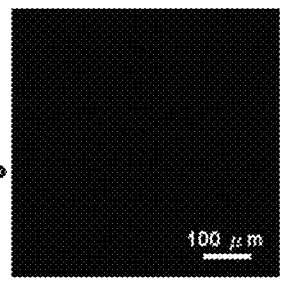

Figure 10-i1

*Bacillus subtilis*

After antibiotic treatment, bacteria coated with Au nanoshells exposed to femtosecond laser

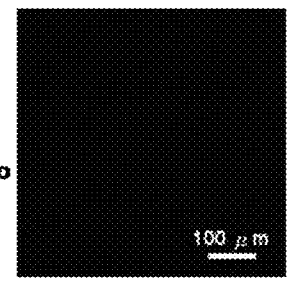

Figure 10-i2

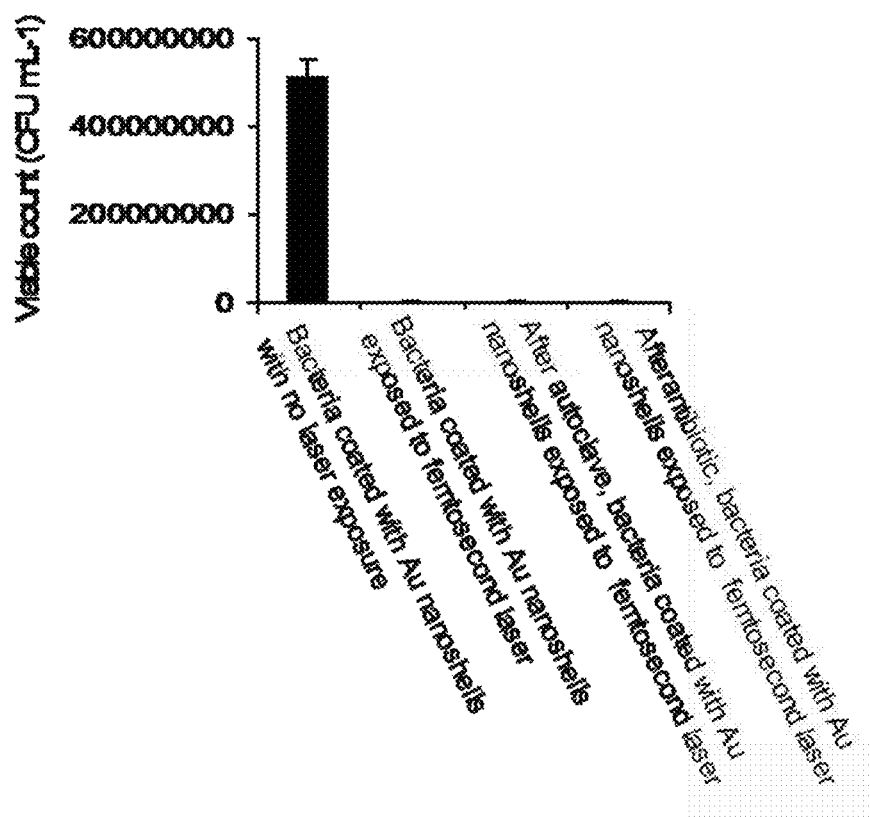
Figure 10-j1

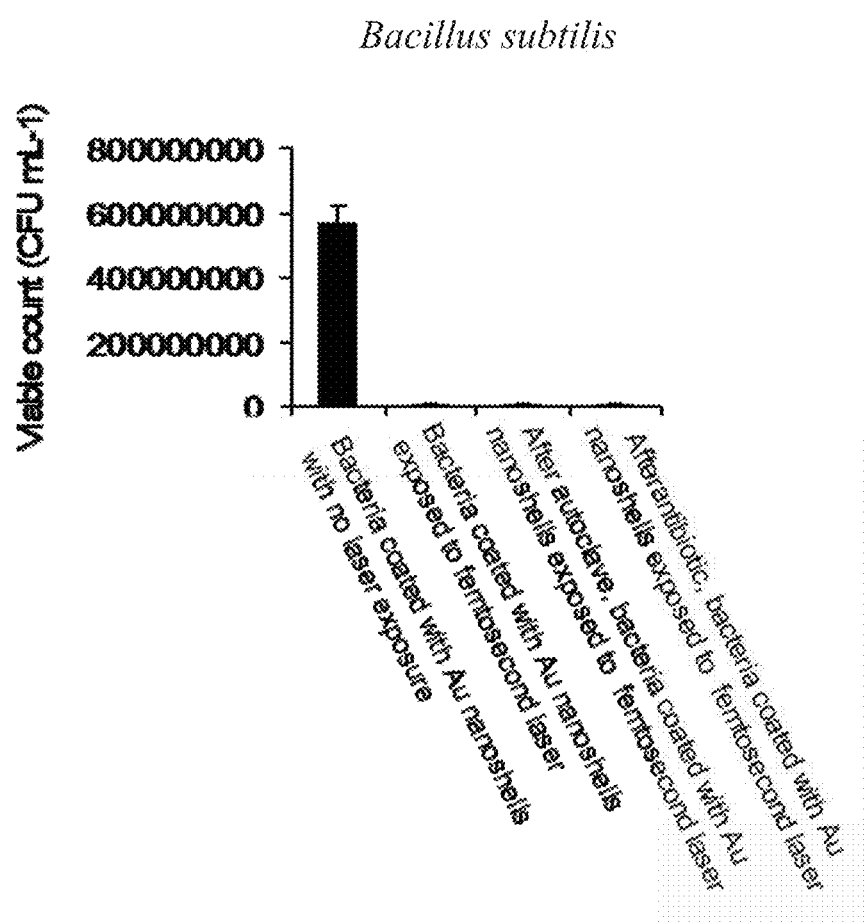
Figure 10-j2

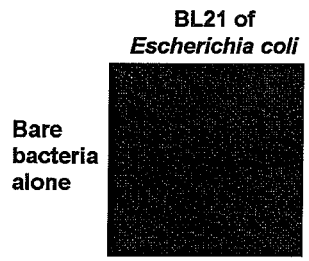
Figure 11-a1
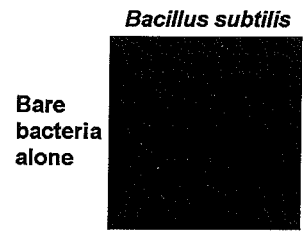
Figure 11-a2
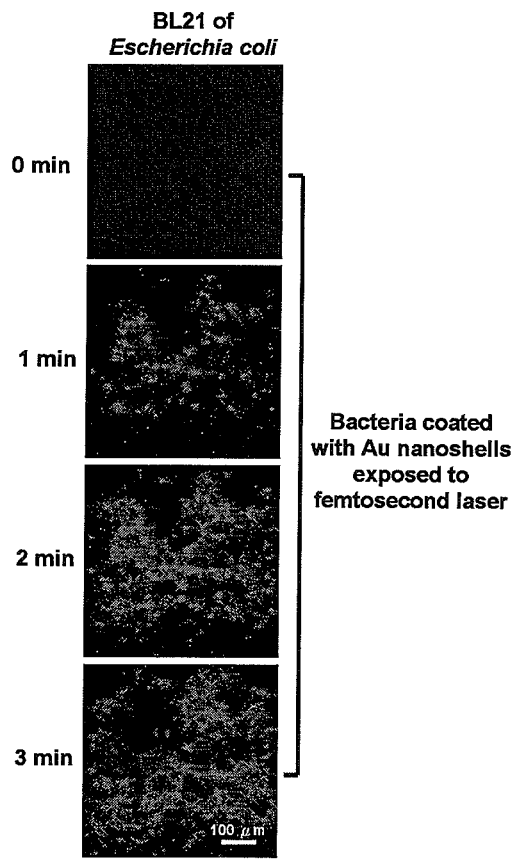
Figure 11-b1
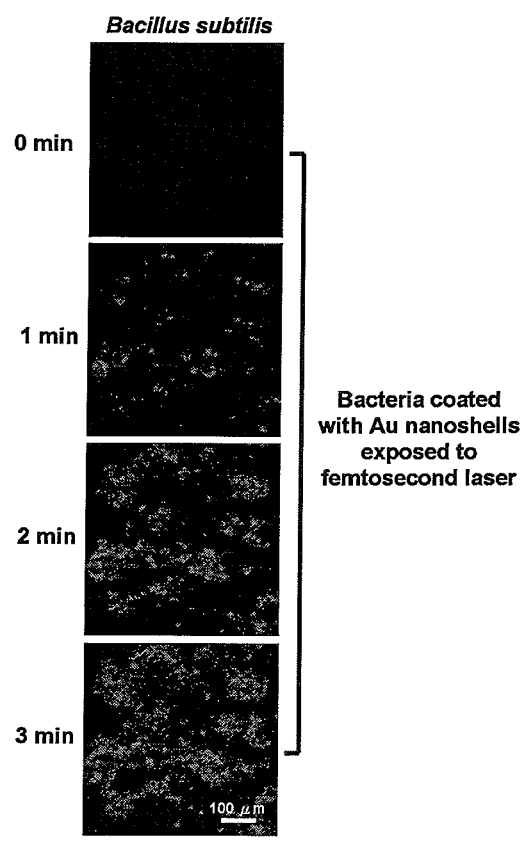
Figure 11-b2

|  | BL21 of *Escherichia coli* | *Bacillus subtilis* |
|---|---|---|
| Bare bacteria alone | 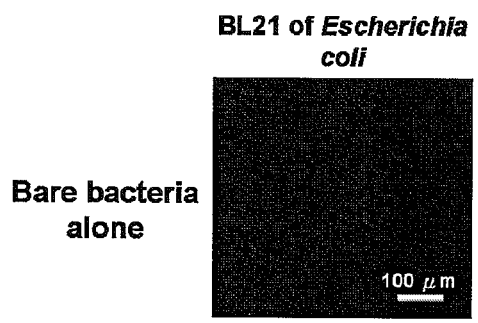<br>Figure 12-a1 | 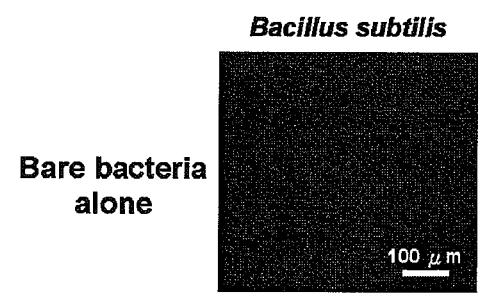<br>Figure 12-a2 |
| Exposed to CW-NIR laser | 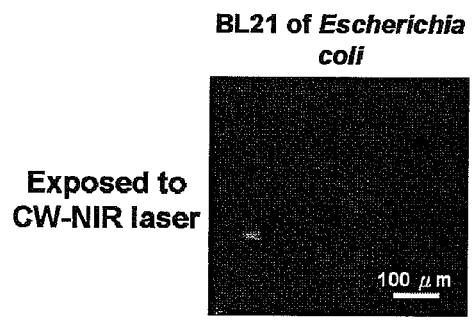<br>Figure 12-b1 | 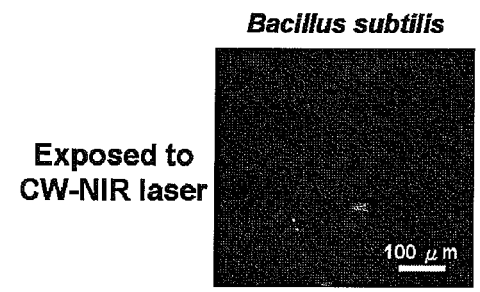<br>Figure 12-b2 |

*Staphyococcus aureus*

Bacteria coated with Au nanoshells with no laser exposure

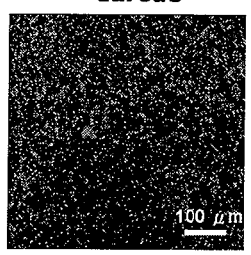

Figure 13-a1

MRSA

Bacteria coated with Au nanoshells with no laser exposure

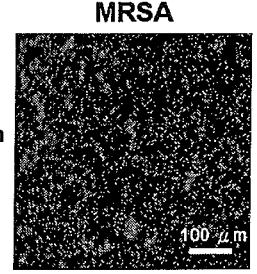

Figure 13-a2

*Staphyococcus aureus*

After vancomycin treatment, bacteria coated with Au nanoshells by no laser exposure

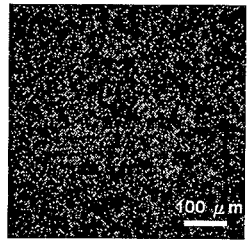

Figure 13-b1

MRSA

After vancomycin treatment, bacteria coated with Au nanoshells by no laser exposure

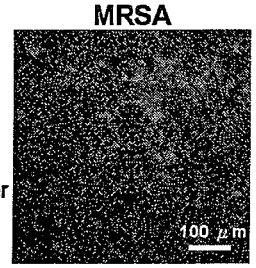

Figure 13-b2

*Staphyococcus aureus*

Bacteria coated with Au nanoshells exposed to CW-NIR laser

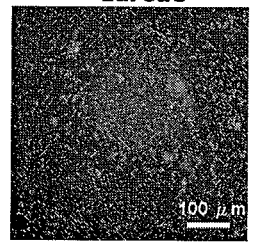

Figure 13-c1

MRSA

Bacteria coated with Au nanoshells exposed to CW-NIR laser

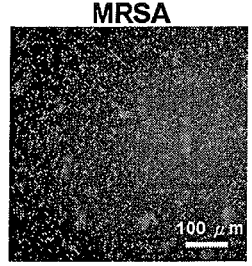

Figure 13-c2

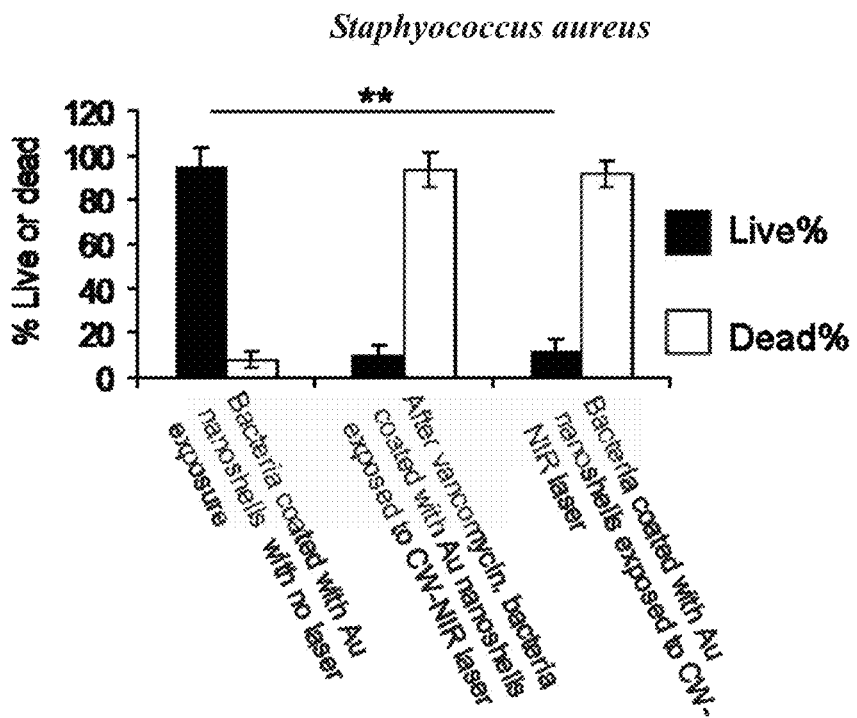
Figure 13-d1
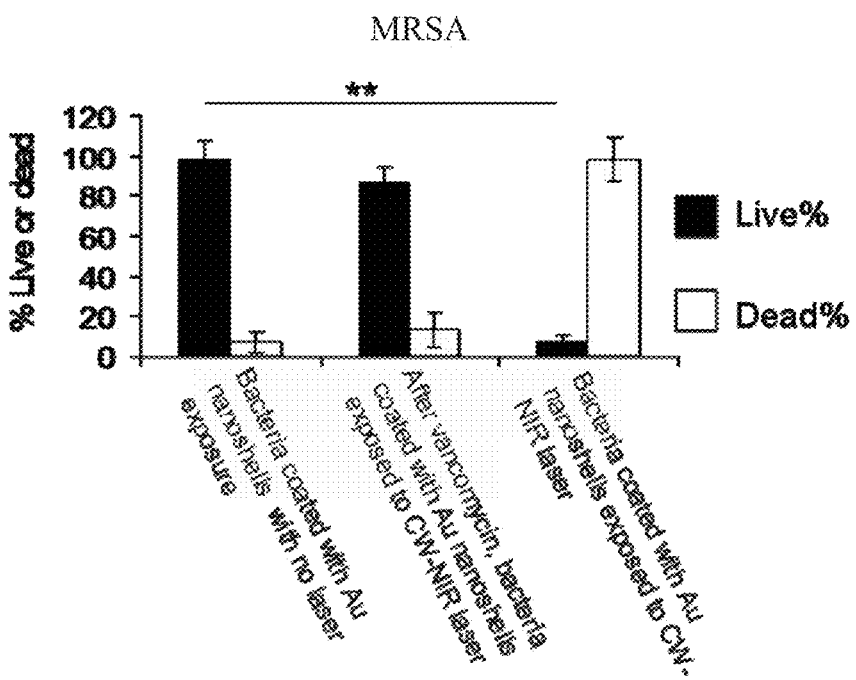
Figure 13-d2

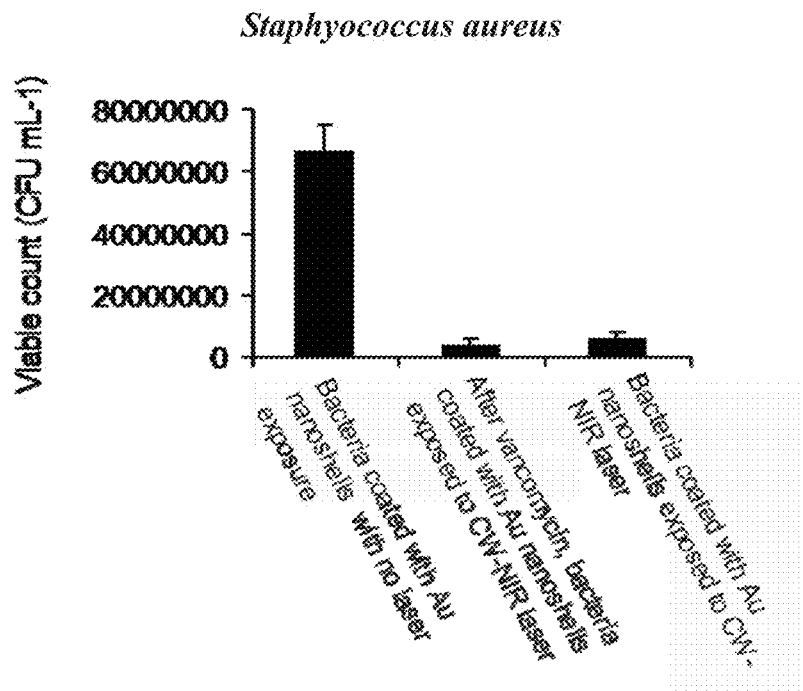
Figure 13-e1
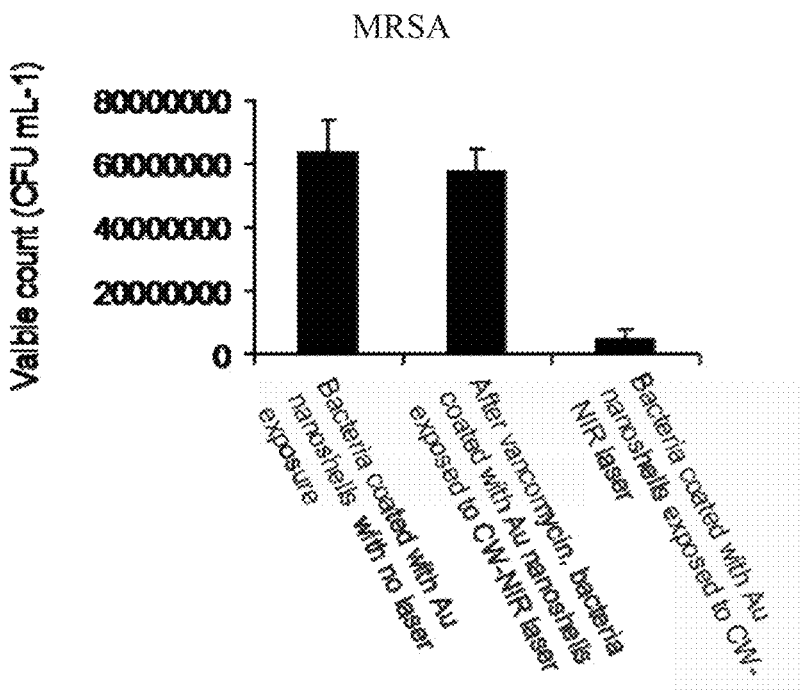
Figure 13-e2

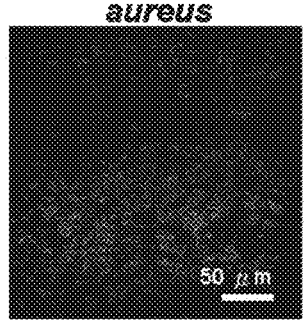
*Staphyococcus aureus*
Bacteria coated with Au nanoshells exposed to femtosecond laser
Figure 13-f1
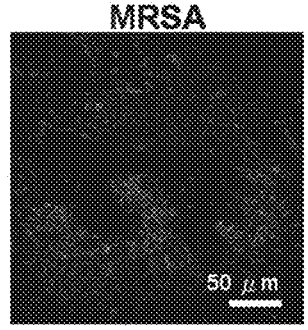
MRSA
Bacteria coated with Au nanoshells exposed to femtosecond laser
Figure 13-f2
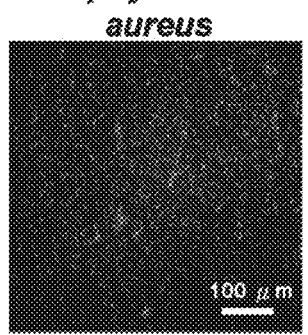
*Staphyococcus aureus*
Bacteria coated with Au nanoshells exposed to femtosecond laser
Figure 13-g1
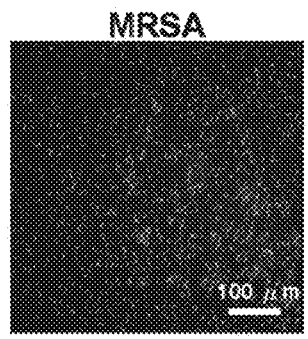
MRSA
Bacteria coated with Au nanoshells exposed to femtosecond laser
Figure 13-g2

*Staphyococcus aureus*
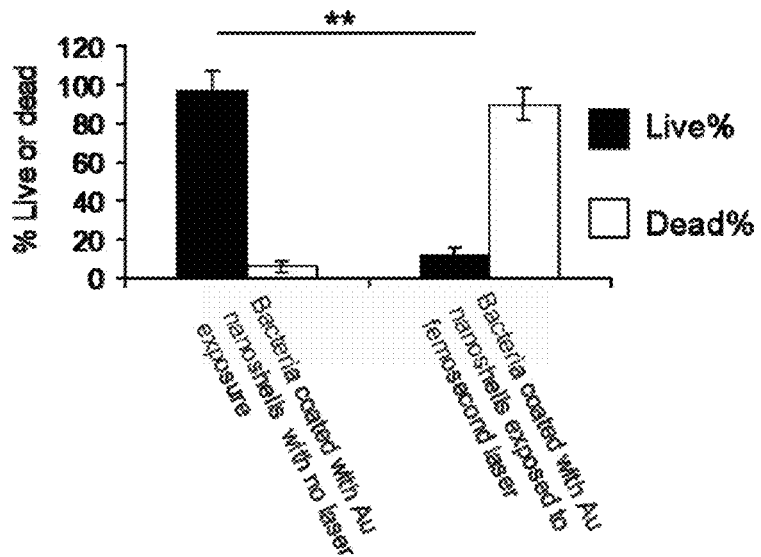
Figure 13-h1
MRSA
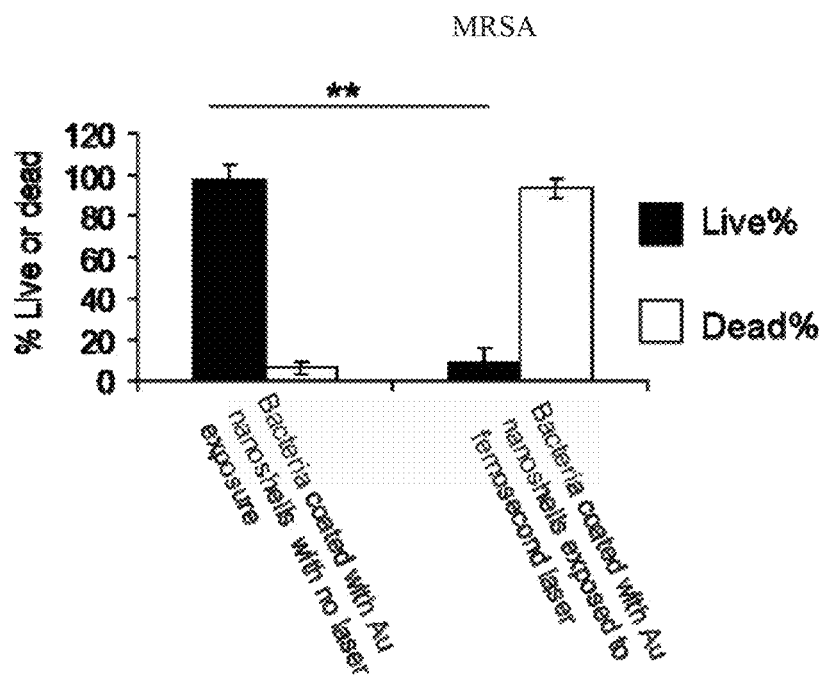
Figure 13-h2

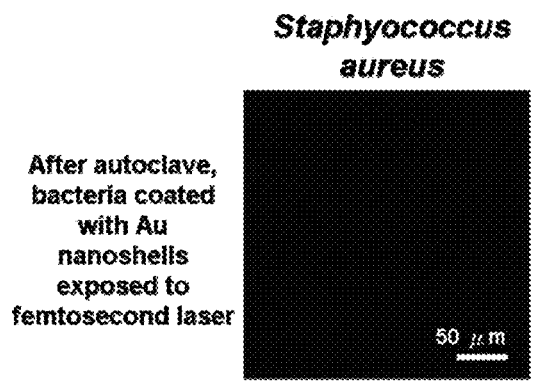

*Staphyococcus aureus*

After autoclave, bacteria coated with Au nanoshells exposed to femtosecond laser 50 μm

Figure 13-i1

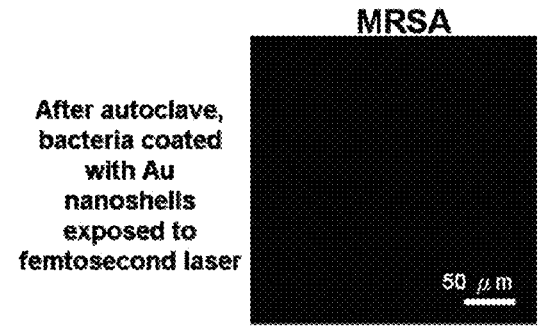

MRSA

After autoclave, bacteria coated with Au nanoshells exposed to femtosecond laser 50 μm

Figure 13-i2

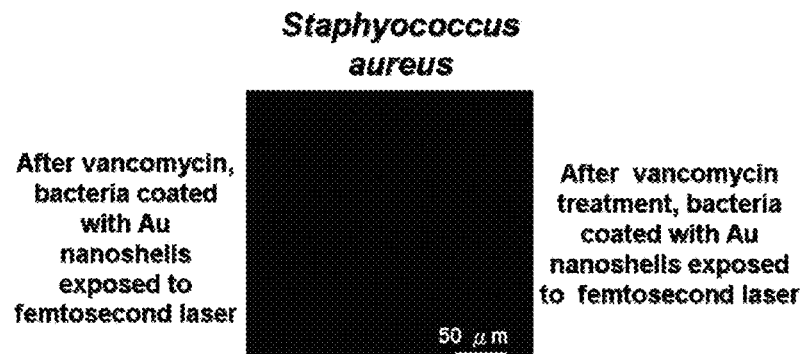

*Staphyococcus aureus*

After vancomycin, bacteria coated with Au nanoshells exposed to femtosecond laser 50 μm

Figure 13-j1

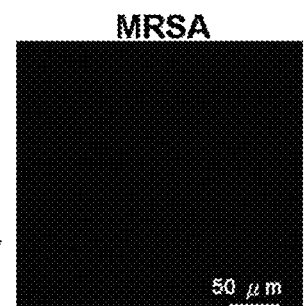

MRSA

After vancomycin treatment, bacteria coated with Au nanoshells exposed to femtosecond laser 50 μm

Figure 13-j2

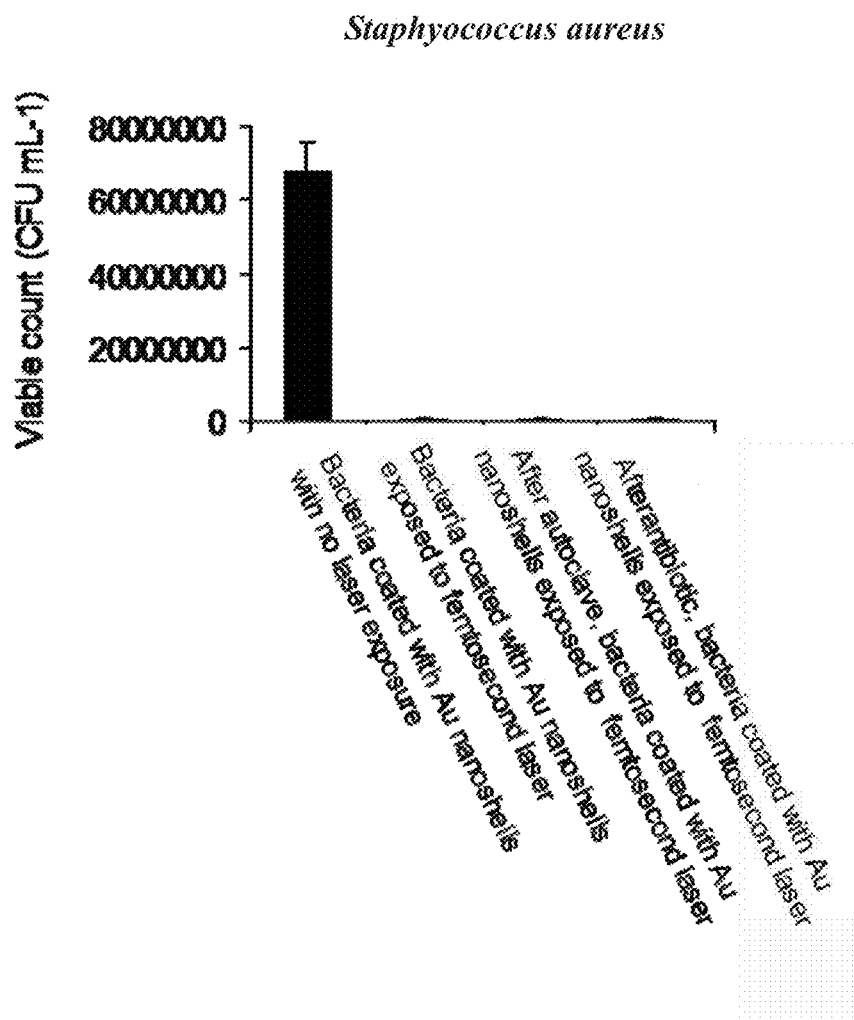
Figure 13-k1

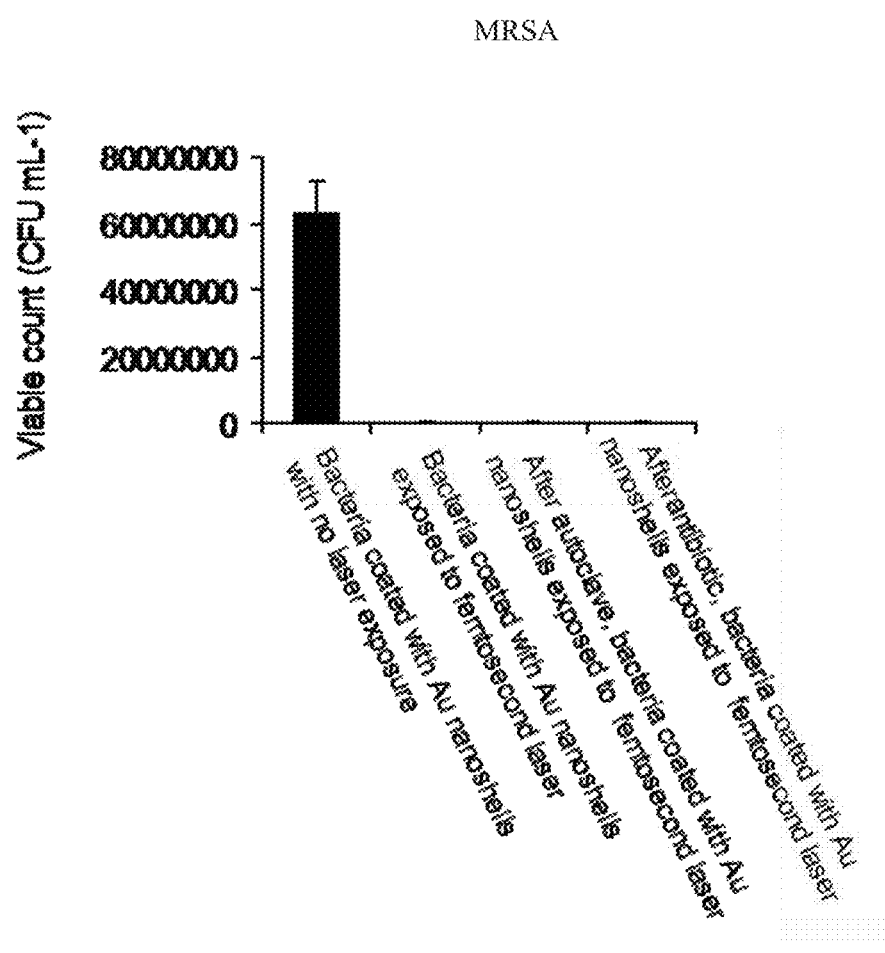
Figure 13-k2

70 mW
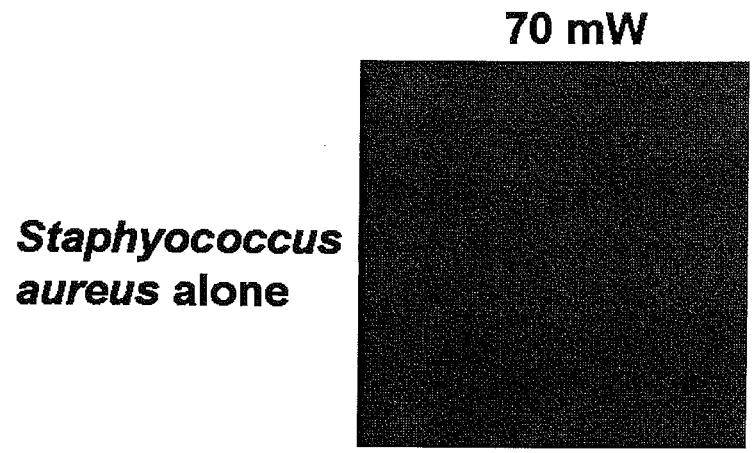
*Staphyococcus aureus* alone
Figure 14-a1
80 mW
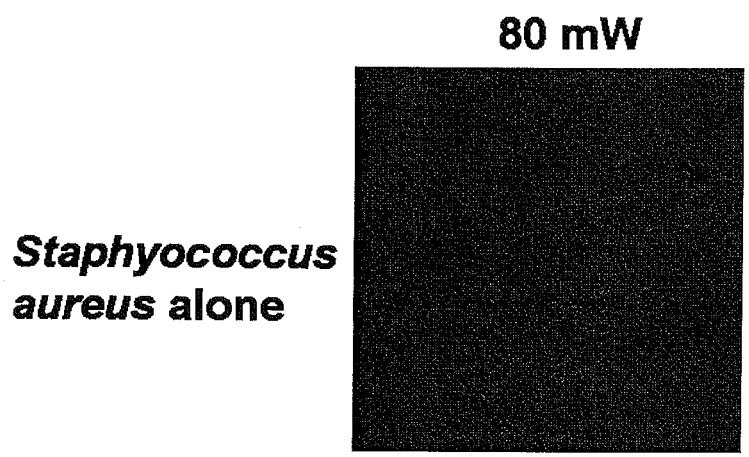
*Staphyococcus aureus* alone
Figure 14-a2
90 mW
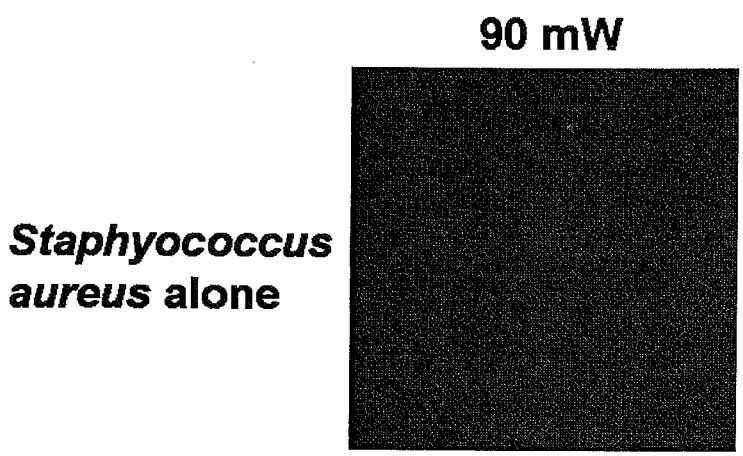
*Staphyococcus aureus* alone
Figure 14-a3

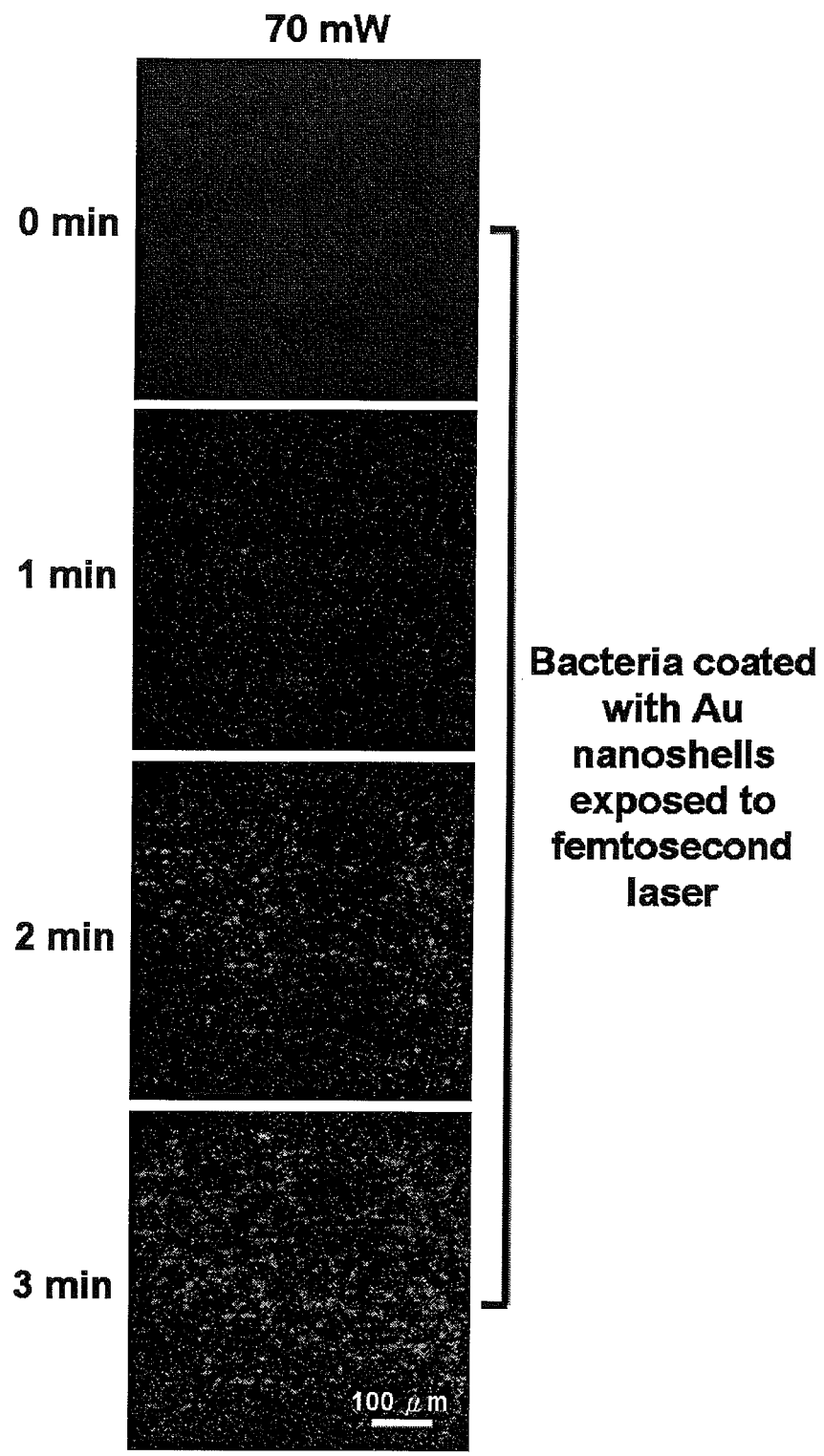
Figure 14-b1

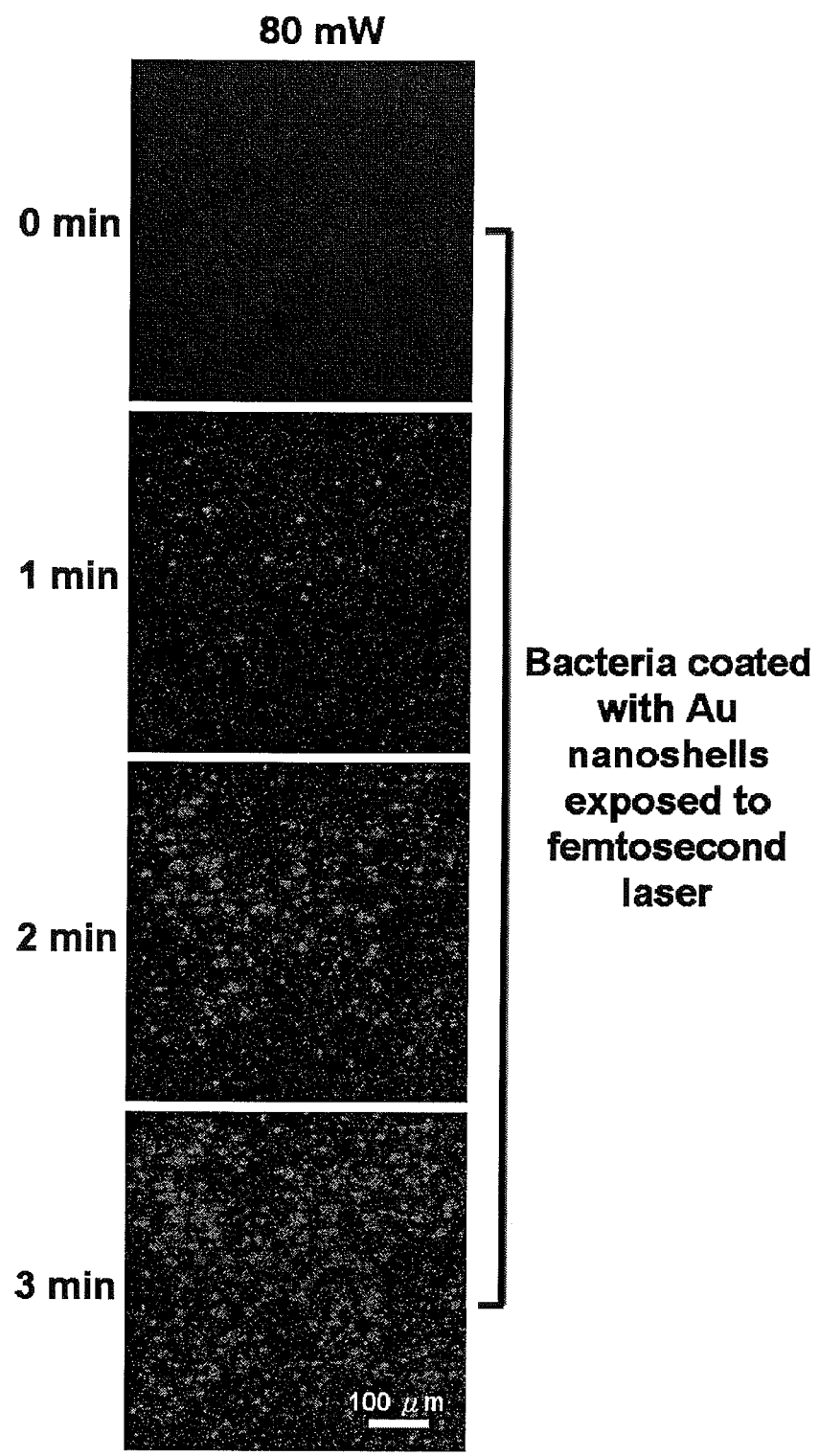
Figure 14-b2

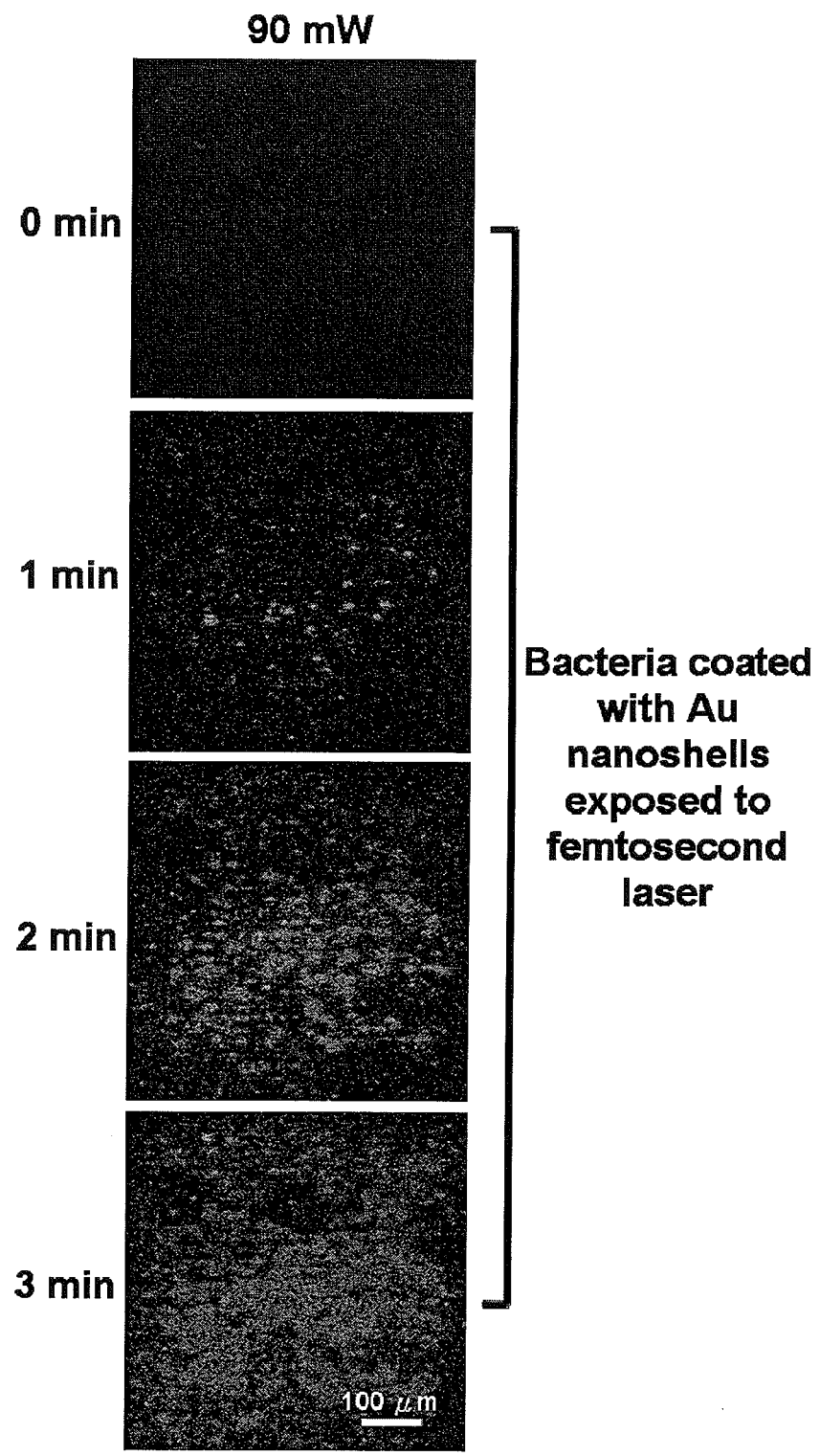
Figure 14-b3

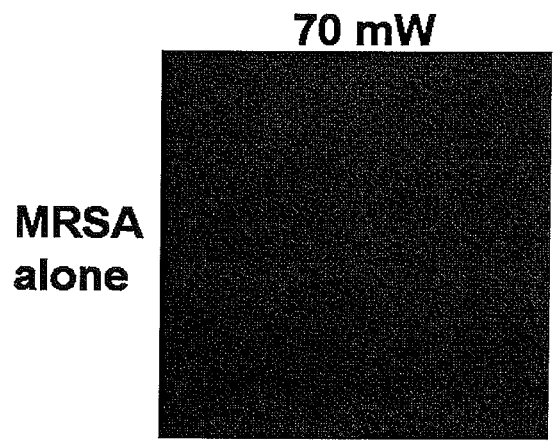
Figure 15-a1
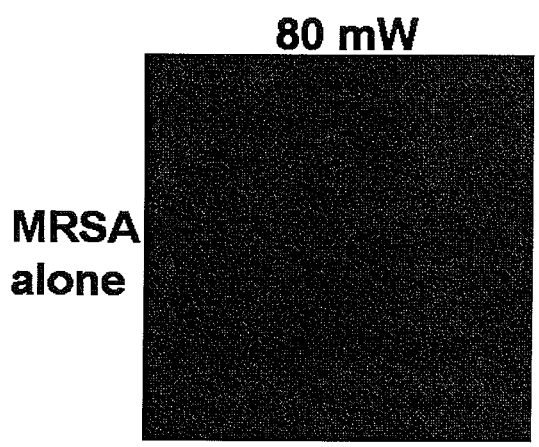
Figure 15-a2
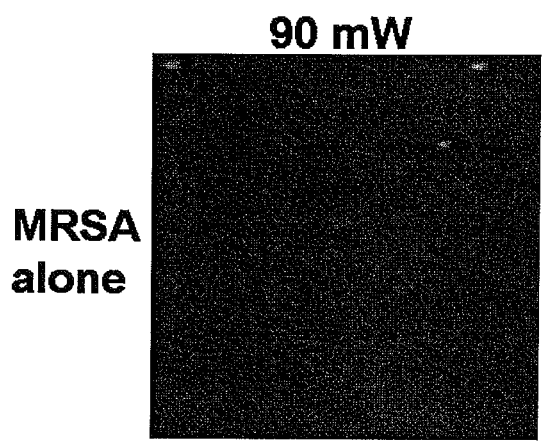
Figure 15-a3

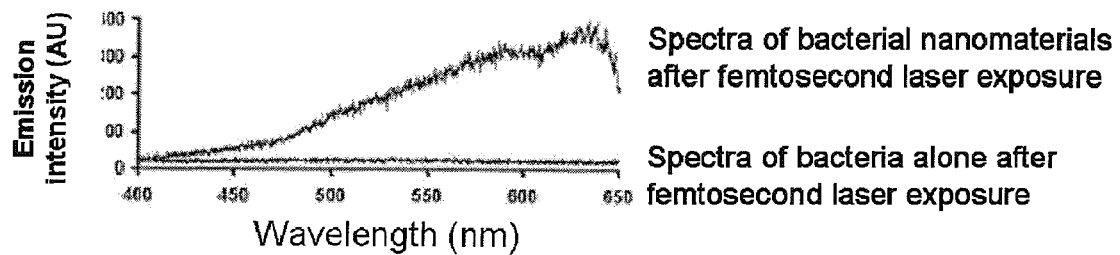
Figure 16-a
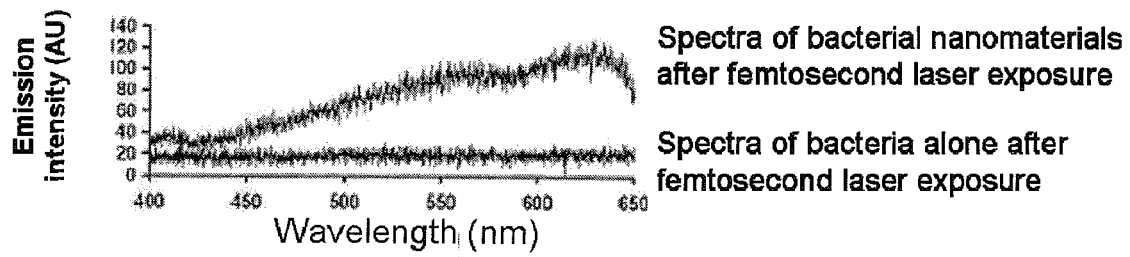
Figure 16-b
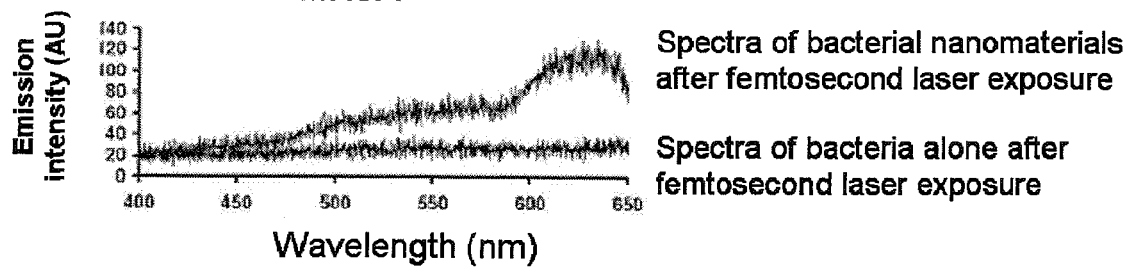
Figure 16-c

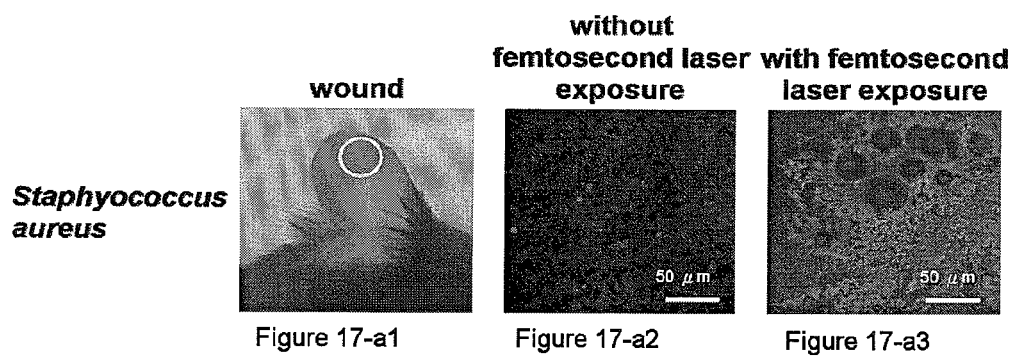
*Staphyococcus aureus*
wound — Figure 17-a1
without femtosecond laser exposure — Figure 17-a2
with femtosecond laser exposure — Figure 17-a3
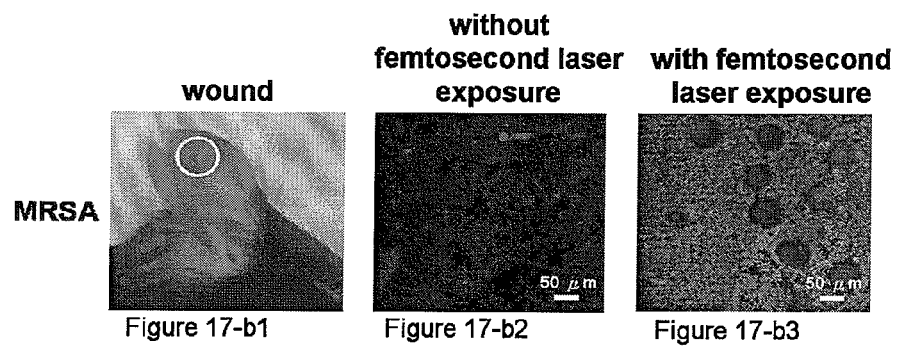
MRSA
wound — Figure 17-b1
without femtosecond laser exposure — Figure 17-b2
with femtosecond laser exposure — Figure 17-b3

METHOD FOR KILLING AND TRACING BACTERIA BY COATING SAME WITH SELF-ASSEMBLED GOLD NANOSHELL LAYER AND PRODUCING PHOTOTHERMAL DECOMPOSITION AND COLD LIGHT BY MEANS OF LASER

CROSS REFERENCE

The present application is a continuation of International Application No. PCT/CN2013/073450 filed Mar. 29, 2013, which is hereby incorporated herein by reference.

BACKGROUND

This invention provides a very easy and simple way to kill and monitor bacteria, and multidrug resistant bacteria in particular.

1. Conventional Ways to Kill Bacteria 1.1 Antibiotics—

A drug is used to treat infections caused from bacteria and other microorganisms. Originally, an antibiotic is a substance produced by one microorganism that selectively inhibits the growth of another. Synthetic antibiotics, usually chemically related to natural antibiotics, have been produced that accomplish comparable tasks. In 1926, Alexander Fleming discovered penicillin, a substance produced by fungi that appeared able to inhibit bacterial growth. In 1939, Edward Chain and Howard Florey further studied penicillin and later carried out trials of penicillin on humans (with what were deemed fatal bacterial infections). Fleming, Florey and Chain shared the Nobel Prize in 1945 for their work which ushered in the era of antibiotics. Another antibiotic, for example, is tetracycline (brand names: Achromycin and Sumycin), a broad-spectrum agent effective against a wide variety of bacteria including *Hemophilus influenzae, Streptococcu pneumoniae, Mycoplasma pneumoniae, Chlamydia psittaci, Chlamydia trachomats, Neisseria* gonorrhoea, and many others. The first drug of the tetracycline family, chlortetracycline, was introduced in 1948.

The most widely known antibiotic is perhaps penicillin, famously made from mold. When it was introduced, many of the sexually transmitted diseases such as gonorrhea went from being a shameful and life changing event to an embarrassing trip to the doctors. One of the most prevalent and unstoppable myths about antibiotics is that they can cure a cold. Antibiotics work against bacterial infections, and colds are caused by viruses—therefore, a course of antibiotics will do nothing but perhaps kill off the body's own population of beneficial bacteria, leaving the cold to run its natural course. Nevertheless, patients often pressure their doctors into prescribing antibiotics when they come down with a cold or the influenza.

1.2 Autoclave—

An autoclave is a device used to sterilize equipment and supplies by subjecting them to high pressure (1.2-1.5 kg $cm^{-2}$) saturated steam at 121° C. for around 15-20 minutes depending on the size of the load and the contents. It was invented by Charles Chamberland in 1879, although a precursor known as the steam digester was created by Denis Papin in 1679. The name comes from Greek auto-, ultimately meaning self, and Latin clavis meaning key—a self-locking device. Autoclaves are widely used in microbiology, medicine, tattooing, body piercing, veterinary science, mycology, dentistry, chiropody and prosthetics fabrication. They vary in size and function depending on the media to be sterilized. Typical loads include laboratory glassware, other equipment and waste, surgical instruments and medical waste. A notable growing application of autoclaves is the pre-disposal treatment and sterilization of waste material, such as pathogenic hospital waste. Machines in this category largely operate under the same principles as conventional autoclaves in that they are able to neutralize potentially infectious agents by utilizing pressurized steam and superheated water. A new generation of waste converters is capable of achieving the same effect without a pressure vessel to sterilize culture media, rubber material, gowns, dressing, gloves, etc. It is particularly useful for materials which cannot withstand the higher temperature of a hot air oven. Autoclaves are also widely used to cure composites and in the vulcanization of rubber. The high heat and pressure that autoclaves allow help to ensure that the best possible physical properties are repeatably attainable.

2. Biological Templates 2.1 Viral Templates—

Viruses are generally composed of proteinaceous shell (capsid) surrounding genomic material. One such template, viruses, exhibits the characteristics of an ideal nanobuilding block, monodispersity, site-specific heterogenerous surface chemistry accessible interior, and extensive chemical tailorability. They offer a suite of beneficial characteristics for the synthesis of metallodielectric nanoshells, including a number of morphologies (spheres, rods, and tubules) that are absolutely monodisperse and both external and internal surfaces that are chemically addressable by a broad range of organic and inorganic chemistries. For example, amino acids on the surface of the capsid, such as cystine, glutamic acid, and aspartic acid, present amine, carboxylate, and thiol groups that are amenable to complexation with metal nanoparticles (NPs). A capsid can also be easily modified to present additional thiol groups on the particle surface.

The use of a virus core and adaptation of the aforementioned chemistries to the growth of metal nanoshells are discussed herein. Utilization of a native virus and the inherent chemical functionality of the capsid affords the ability to grow and harvest biotemplates in large quantities. These natural templates simplify the preparation of the dielectric core particle and provide a narrower size distribution and accessible core sizes below 80 nm. Furthermore, upon removal of the core genetic material, the resultant virus-like particle provides a hollow shell, enabling facile incorporation of various electrooptic molecules within the center of the nanoshell and thus accessing the local field enhancements within as well as at the surface of the nanoshell.

Toward these objectives, the first metallic nanoshells based on bioscaffolds are produced using *Chilo iridescent* virus (CIV) as the dielectric core. In 2005, Radloff et. al. utilized CIV to demonstrated as a useful core substrate in the fabrication of metallo dielectric, plasmonic nanostructures. An gold (Au) shell is assembled around the wild-type viral core by attaching small NPs to the virus surface by means of the chemical functionality found inherently on the surface of the proteinaceous viral capsid. The density of these nucleation sites was maximized by reducing the repulsive forces between the Au particles through electrolyte addition. These Au NPs then act as nucleation sites for the electroless deposition of Au ions from solution around the biotemplate. The optical extinction spectra of the metalloviral complex is in quantitative agreement with Mie scattering theory. Overall, the utilization of a native virus and the inherent chemical functionality of the capsid afford the ability to grow and harvest biotemplates for metallodielectric nanoshells in large quantities, potentially providing cores with a narrower size distribution and smaller diameters (below 80 urn) than for currently used silica.

Au shell growth around CIV cores is demonstrated using modifications to previous established fabrication routes. By decreasing the surface charge of the capsid through controlled introduction of excess electrolyte, maximization of the non-selective attachment of Au NPs to the capsid surface enabled the growth of a complete Au shell around CIV. The resulting metallodielectric nanoshell exhibited a dipole resonance in the near infrared region. The inherent surface chemistries of the wild-type viral capsid of CIV enabled a facile fabrication route for metallodielectric assembly. This is in contrast to virus-like particles where genetic engineering of the capsid and subsequent protein expression and assembly limit scaffold supply and significantly increase preparation and processing concerns. More extensive understanding of the amino acid distribution on the viral surface of the chosen capsid, rather than site-specific mutation, will improve the ability to form smooth shells through use of specific rather than non-specific seed-capsid interaction.

2.2 Fungous Templates—

Micro-organisms, including viruses, bacteria, and fungi, grow into unique and structurally interesting forms that have been used by many researchers as templates for the self-organization of inorganic materials with the aim of realizing functional macrostructures. In such assemblies, the inherent uniformity of the biological structures can be combined with the functional properties of inorganic NPs (such as conductivity and optical activity) to realize functional macrostructures. As an example, a dense assembly of NPs on filamentous fungi, with typical hyphal diameters of the order of a few micrometers (varying from species to species) and lengths varying from tens of micrometers to a few millimeters could find immediate applications as circuit components. Most reports on the assembly of inorganic materials on micro-organisms such as viruses, bacteria, and fungi involve complex biological molecules, for example DNA or proteins, facilitating their attachment to the biological surface, either by the sequence-specific recognition properties of DNA strands, or protein recognition.

In 2007, Sugunan et. al. reported a facile route, based on simpler chemistries, for the self-organization of colloidal Au NPs on living filamentous fungi to fabricate Au microstructures with typical widths of several micrometers and lengths exceeding a few millimeters. The process involves synthesis of Au NPs using monosodium glutamate to reduce chloroauric acid, resulting in the formation of colloidal particles stabilized by glutamate ions. Fungal conidia are then added and allowed to grow in the colloidal medium. The physiological process of absorption of nutrients by the fungus, consisting mainly of unreacted precursors (excess glutamate ions) from the reduction-precipitation reaction for the synthesis of the Au NPs, drives the assembly of the NPs. The agglomeration and accumulation of colloidal NPs lead to the formation of a thick coating on the hyphal walls, which exhibit the optical properties of bulk gold. The assemblies so formed can be then modified into micro-ribbon-like and microtubular morphologies by post-fabrication treatment.

This process of self-assembly of NPs on growing filamentous fungi has the potential to be extended to other NPs and micro-organisms. In principle, any micro-organism that can survive on simple nutrients (such as bacteria, which can survive with only glutamates as nourishment) can act as templates, while the weak ligand-particle interaction (typical for charge-stabilized NPs of any material) and the consequent sensitivity to the ionic content in the dispersant medium can drive the organized agglomeration. Thus, by engineering the dispersant solution with the required nutrients, the described process has the potential to be extended to the self-assembly of chargestabilized colloidal NPs of a wide range of materials into novel structures, utilizing the symmetry and structural shapes dictated by micro-organisms.

2.3 Bacterial Templates—

Bacteria constitute a large domain of prokaryotic microorganisms. Typically a few micrometers in length, bacteria have a wide range of shapes, ranging from spheres to rods and spirals. There are broadly speaking two different types of cell wall in bacteria, called Gram-positive and Gram-negative. The following characteristics are generally present in a Gram-positive bacterium, a. cytoplasmic lipid membrane; b. thick peptidoglycan layer: teichoic acids and lipoids are present, forming lipoteichoic acids, which serve to act as chelating agents, and also for certain types of adherence; c. capsule polysaccharides (only in some species); d. flagellum (only in some species), if present, it contains two rings for support as opposed to four in Gram-negative bacteria because Gram-positive bacteria have only one membrane layer. e. The individual peptidoglycan molecules are cross-linked by pentaglycine chains by a DD-transpeptidase enzyme. In Gram-negative bacteria, the transpeptidase creates a covalent bond directly between peptidoglycan molecules, with no intervening bridge. On the other hand, Gram-negative bacteria was displayed some characteristics as follows, a). cytoplasmic membrane; b). thin peptidoglycan layer (which is much thicker in Gram-positive bacteria); c). outer membrane containing lipopolysaccharide (LPS, which consists of lipid A, core polysaccharide, and O antigen) in its outer leaflet and phospholipids in the inner leaflet; d). porins exist in the outer membrane, which act like pores for particular molecules; e). there is a space between the layers of peptidoglycan and the secondary cell membrane called the periplasmic space; f). the S-layer is directly attached to the outer membrane, rather than the peptidoglycan; if present, flagella have four supporting rings instead of two; g). no teichoic acids or lipoteichoic acids are present; h). lipoproteins are attached to the polysaccharide backbone; i). most of them contain Braun's lipoprotein, which serves as a link between the outer membrane and the peptidoglycan chain by a covalent bond; j). most do not sporulate.

Bacteria could be of help or endanger to human being, animals and environment. It is known that bacteria could be utilized to cure some diseases and ailments, for instance, cloning of molecular biology, photo synthetic bacteria, etc. However, the interaction of Au with the systems of microorganism has been a topic of interest in widely divergent fields. Integrating biology into materials research to bring forward significant advances in microfabrication resulting in functional structures at the nano-, and micro-scale is still under research.

SUMMARY

Preparing Au NPs coated bacteria as well as using them to destroy and lyse bacteria is a novel concept in nanoscience. Gram-negative bacteria of *Escherichia coli* (*E. coli*) BL21, and Gram-positive bacteria of *Bacillus subtilis, Staphylococcus aureus* and methicillin-resistant *Staphylococcus aureus* (MRSA) were utilized as biologcal templates. Specially, no adding reductant, and sequentially the Au NPs grew self-assembling to yield Au nanoshells on the surface of bacteria. The same reaction mechanism would happen in all metallic ion-containing solution to form metallic shell on the bacterial surface. The active driving force for oxidation and reduction on the bacterial surface might be derived from the crystalline surface layer (S-layer) of bacteria. The bacteria with Au nanoshells still kept their vitality and mobility.

We have successfully converted infectious bacteria into a photothermolytic platform that transforms them into a weapon for photothermolytic antimicrobial therapy. The bacteria remained alive under the Au nanoshell coating, even after the incubation in the solutions had been extended to several weeks. Furthermore, the bacteria coated Au nanoshells could probe for promising bacteria detection by combining biological microorganisms with the linear and nonlinear optical properties of Au NPs due to Au with the high efficiency to convert absorbed radiation into heat.

Bacteria coated with Au nanoshells exhibited absorption in the near infrared (NIR) window by one-photon excitation as well as the good absorption in the NIR window by monitoring the relative two-photon absorption (TPA) spectrum of the bacteria coated with Au nanoshells.

Bacterial nanomaterials (or called bacteria coated with Au nanoshells) showed impressive photothermolytic efficacy to reduce the viability of bacteria with laser irradiation, and furthermore an excellent ability to emit photoluminescence after laser irradiation which was generated from the dead bacteria coated with Au nanoshells. Bacterial nanomaterials that possessed the intrinsic photo-property had the capability to emit photoluminescence with laser exposure. The more bacteria were dead, the stronger emission to a saturated intensity was with the increase of exposing time. The same phenomenon would happen in all metallic shell on the bacterial surface and noble metal shell on the bacterial surface in particular. Furthermore, the photoluminescence in this invention which was able to sustain femtosecond laser exposure, keep luminescence emitted and prevent from photobleaching was still generated after long-term exposure being very qualified to optical contrast agents.

In order to compare with other different treatments, results showed there was no lei photoluminescence emitted from bacterial nanomaterials after the treatments of autoclave and antibiotics.

In vivo experiment, the Au nanoshells were also able to be coated on bacterial surface in the wound of mouse's ear, and this exhibited outstandingly antimicrobial efficacy. The bacterial nanomaterials that were definitely able to serve as a brand-new contrast agent to determine whether the bacteria were alive or not and to track and localize the bacteria by emitted photoluminescence, and this new weapon still provided us a new view to handle and manipulate bacteria into biomedical applications.

The multidrug-resistant (MDR) bacterial strains have been a serious medical problem. MRSA are resistant to many antibiotics and are often associated with several diseases such as arthritis, osteomyelitis, and endocarditis. There has been a great interest to develop alternative treatment to eliminate multidrug-resistant bacteria, i.e. MRSA. These nanomaterials were definitely able to serve as brand-new contrast agents or indicators to determine viability of bacteria and to track and localize the bacteria by emitted photoluminescence. These results might provide us a new view to handle and manipulate bacteria into clinical applications.

DESCRIPTION OF THE DRAWINGS

FIG. 3-$b$ shows images of Au nanoshells formed on the surface of E. coli (BL21) and characterized by TEM.

FIG. 3-$c$ shows images of HAADF STEM successfully utilized to determine the self-assembling Au nanoshells on the surface of E. coli (BL21).

FIG. 3-$d$ shows images of Bacillus subtilis without Au nanoshells characterized by TEM.

FIG. 3-$e$ shows images of Au nanoshells formed on the surface of Bacillus subtilis and characterized by TEM.

FIG. 3-$f$ shows images of HAADF STEM successfully utilized to determine the self-assembling Au nanoshells on the surface of Bacillus subtilis.

FIG. 3-$g$ shows images of MRSA without Au nanoshells characterized by TEM.

FIG. 3-$h$ shows images of Au nanoshells formed on the surface of MRSA and characterized by TEM.

FIG. 3-$i$ shows images of HAADF STEM successfully utilized to determine the self-assembling Au nanoshells on the surface of MRSA.

FIG. 4-$a$ shows a Fourier transform infrared (FTIR) spectra of bacteria with or without Au nanoshells. (a) Bare E. coli (BL21) showed the strong band of O—H coupled with C—O, the O—C=C asymmetric stretching and the symmetric carboxyl ion $C(=O)_2$ stretching of the amino acid side chain, respectively. After the Au nanoshells formation, the bands mentioned above disappeared or were shifted to a longer wavelength.

FIG. 4-$b$ shows a FTIR spectra of bacteria with or without Au nanoshells. Bare Bacillus subtilis presented O—C=C asymmetric stretching and amino acid stretching, respectively. After the Au nanoshells formation, the bands mentioned above disappeared or were shifted to a longer wavelength.

FIG. 4-$c$ shows a FTIR spectra of bacteria with or without Au nanoshells. Bare MRSA had the O—C=C asymmetric and amino acid stretching, respectively. After the Au nanoshells formation, the bands mentioned above disappeared or were shifted to a longer wavelength.

FIG. 5$a$-1 shows X-ray diffraction (XRD) analysis of Au nanoshells derived from E. coli (BL21).

FIG. 5$a$-2 shows energy-dispersive X-ray spectroscopy (EDX) analysis of Au nanoshells derived from E. coli (BL21).

FIG. 5$b$-1 shows XRD analysis of Au nanoshells derived from Bacillus subtilis.

FIG. 5$b$-2 shows EDX analysis of Au nanoshells derived from Bacillus subtilis.

FIG. 5$c$-1 shows XRD analysis of Au nanoshells derived from MRSA.

FIG. 5$c$-2 shows EDX analysis of Au nanoshells derived from MRSA.

FIG. 6-$a$ shows the Au-ion binding and Au NPs formation efficiency as a function of incubation time.

FIG. 6-$b$ shows images of third harmonic generation (THG). E. coli (BL21) coated with nanoshells showed the THG images of bacteria at different time periods (taken from a time series of the THG image) using a femtosecond Cr:forsterite laser microscopy. In these figures, both the morphology and the movement (according to the arrows) of E. coli (BL21) were revealed with submicron lateral resolution.

FIG. 6-$c$ shows a fluorescence micrograph of BL21 coated with Au nanoshells, stained with a LIVE (SYTO 9)/DEAD (propidium iodide) kit and observed using fluorescence microscopy.

FIG. 6-d shows a TEM image showing after long-term incubation, the bacteria, E. coli (BL21), undergoing growth and division still even though coated with Au nanoshells. At the same time, there were some aggregated and large impurities adhered to or around the nanoshells.

FIG. 6-e shows a TEM image showing after long-term incubation, the bacteria, *Bacillus subtilis*, undergoing growth and division still even though coated with Au nanoshells. At the same time, there were some aggregated and large impurities adhered to or around the nanoshells.

FIG. 6-f shows a TEM image showing after long-term incubation, the bacteria, MRSA, undergoing growth and division still even though coated with Au nanoshells. At the same time, there were some aggregated and large impurities adhered to or around the nanoshells.

FIG. 7-a shows UV/Visible absorbance as a function of incubation time between E. coli (BL21) with the solution contained Au ion monitored for the evolution of Au NPs, respectively.

FIG. 7-b shows UV/Visible absorbance as a function of incubation time between *Bacillus subtilis* with the solution contained Au ion monitored for the evolution of Au NPs, respectively.

FIG. 7-c shows UV/Visible absorbance as a function of incubation time between MRSA with the solution contained Au ion monitored for the evolution of Au NPs, respectively.

FIG. 8-a shows the temperature dependence of continuous wave (CW)-NIR-irradiated water, E. coli (BL21) coated with Au nanoshells, as a function of irradiation time.

FIG. 8-b shows the temperature dependence of continuous wave (CW)-NIR-irradiated water, *Bacillus subtilis* coated with Au nanoshells, as a function of irradiation time.

FIG. 8-c shows the temperature dependence of continuous wave (CW)-NIR-irradiated water, MRSA coated with Au nanoshells, as a function of irradiation time.

FIG. 10-a1 shows images of E. coli (BL21) coated with Au nanoshells without CW-NIR laser exposure were stained with a LIVE/DEAD kit and observed using fluorescence microscopy.

FIG. 10-a2 shows images of *Bacillus subtilis* coated with Au nanoshells without CW-NIR laser exposure were stained with a LIVE/DEAD kit and observed using fluorescence microscopy.

FIG. 10-b1 shows images of E. coli (BL21) coated with Au nanoshells by CW-NIR linear laser exposure were stained with a LIVE/DEAD kit and observed using fluorescence microscopy.

FIG. 10-b2 shows images of *Bacillus subtilis* coated with Au nanoshells by CW-NIR linear laser exposure were stained with a LIVE/DEAD kit and observed using fluorescence microscopy.

FIG. 10-c1 shows a viability estimation of FIGS. 10-a1 and 10-b1 quantified.

FIG. 10-c2 shows a viability estimation of FIGS. 10-a2 and 10-b2 quantified.

FIG. 10-d1 shows the CFU viability test of FIGS. 10-a1 and 10-b1 quantified.

FIG. 10-d2 shows the CFU viability test of FIGS. 10-a2 and 10-b2 quantified.

FIG. 10-e1 shows images of E. coli (BL21) coated with Au nanoshells by the exposure of two-photon femtosecond Ti:sapphire nonlinear laser.

FIG. 10-e2 shows images of *Bacillus subtilis* coated with Au nanoshells by the exposure of two-photon femtosecond Ti:sapphire nonlinear laser.

FIG. 10-f1 shows images of E. coli (BL21) coated with Au nanoshells by the exposure of two-photon femtosecond Ti:sapphire nonlinear laser, then stained with a LIVE/DEAD kit and observed using fluorescence microscopy.

FIG. 10-f2 shows images of *Bacillus subtilis* coated with Au nanoshells by the exposure of two-photon femtosecond Ti:sapphire nonlinear laser, then stained with a LIVE/DEAD kit and observed using fluorescence microscopy.

FIG. 10-g1 shows the viability estimation of FIGS. 10-a1 and 10-f1 quantified.

FIG. 10-g2 shows the viability estimation of FIGS. 10-a2 and 10-f2 quantified.

FIG. 10-h1 shows images of E. coli (BL21) coated with Au nanoshells treated with autoclave and then exposed to femtosecond nonlinear laser.

FIG. 10-h2 shows images of *Bacillus subtilis* coated with Au nanoshells treated with autoclave and then exposed to femtosecond nonlinear laser.

FIG. 10-i1 shows images of E. coli (BL21) coated with Au nanoshells treated with ampicillin and then exposed to femtosecond nonlinear laser.

FIG. 10-i2 shows images of *Bacillus subtilis* coated with Au nanoshells treated with ampicillin and then exposed to femtosecond nonlinear laser.

FIG. 10-j1 shows the CFU viability test of FIGS. 10-a1, 10-f1, 10-h1 and 10-i1 quantified.

FIG. 10-j2 shows the CFU viability test of FIGS. 10-a2, 10-f2, 10-h2 and 10-i2 quantified.

FIG. 11-a1 shows images of E. coli (BL21) alone after they had been exposed to femtosecond Ti:sapphire nonlinear laser.

FIG. 11-a2 shows images of *Bacillus subtilis* alone after they had been exposed to femtosecond Ti:sapphire nonlinear laser.

FIG. 11-b1 shows images of E. coli (BL21) coated with Au nanoshells after they had been exposed to femtosecond Ti:sapphire nonlinear laser.

FIG. 11-b2 shows images of *Bacillus subtilis* coated with Au nanoshells after they had been exposed to femtosecond Ti:sapphire nonlinear laser.

FIG. 12-a1 shows images of E. coli (BL21) alone after they had been exposed to CW-NIR linear laser.

FIG. 12-a2 shows images of *Bacillus subtilis* alone after they had been exposed to CW-NIR linear laser.

FIG. 12-b1 shows images of E. coli (BL21) coated with Au nanoshells after they had been exposed to CW-NIR linear laser.

FIG. 12-b2 shows images of *Bacillus subtilis* coated with Au nanoshells after they had been exposed to CW-NIR linear laser.

FIG. 13-a1 shows images of *Staphylococcus aureus* coated with Au nanoshells without laser exposure, stained with a LIVE/DEAD kit and observed using fluorescence microscopy.

FIG. 13-a2 shows images of MRSA coated with Au nanoshells without laser exposure, stained with a LIVE/DEAD kit and observed using fluorescence microscopy.

FIG. 13-b1 shows images of *Staphylococcus aureus* coated with Au nanoshells by vancomycin treatment, stained with a LIVE/DEAD kit and observed using fluorescence microscopy.

FIG. 13-b2 shows images of MRSA coated with Au nanoshells by vancomycin treatment, stained with a LIVE/DEAD kit and observed using fluorescence microscopy.

FIG. 13-c1 shows images of *Staphylococcus aureus* coated with Au nanoshells by CW-NIR linear laser exposure, stained with a LIVE/DEAD kit and observed using fluorescence microscopy.

FIG. 13-c2 shows images of MRSA coated with Au nanoshells by CW-NIR linear laser exposure, stained with a LIVE/DEAD kit and observed using fluorescence microscopy.

FIG. 13-d1 shows the viability estimation of FIGS. 13-a1, 13-b1 and 13-c1 quantified.

FIG. 13-d2 shows the viability estimation of FIGS. 13-a2, 13-b2 and 13-c2 quantified.

FIG. 13-e1 shows the CFU viability test of FIGS. 13-a1, 13-b1 and 13-c1 quantified.

FIG. 13-e2 shows the CFU viability test of FIGS. 13-a2, 13-b2 and 13-c2 quantified.

FIG. 13-f1 shows images of *Staphylococcus aureus* coated with Au nanoshells by the exposure of two-photon femtosecond Ti:sapphire nonlinear laser.

FIG. 13-f2 shows images of MRSA coated with Au nanoshells by the exposure of two-photon femtosecond Ti:sapphire nonlinear laser.

FIG. 13-g1 shows images of *Staphylococcus aureus* coated with Au nanoshells by the exposure of two-photon femtosecond Ti:sapphire nonlinear laser, stained with a LIVE/DEAD kit and observed using fluorescence microscopy.

FIG. 13-g2 shows images of MRSA coated with Au nanoshells by the exposure of two-photon femtosecond Ti:sapphire nonlinear laser, stained with a LIVE/DEAD kit and observed using fluorescence microscopy.

FIG. 13-h1 shows the viability estimation of FIGS. 13-a1 and 13-g1 quantified.

FIG. 13-h2 shows the viability estimation of FIGS. 13-a2 and 13-g2 quantified.

FIG. 13-i1 shows images of *Staphylococcus aureus* coated with Au nanoshells by autoclave treatment and then with the exposure of two-photon femtosecond Ti:sapphire nonlinear laser.

FIG. 13-i2 shows images of MRSA coated with Au nanoshells by autoclave treatment and then with the exposure of two-photon femtosecond Ti:sapphire nonlinear laser.

FIG. 13-j1 shows images of *Staphylococcus aureus* coated with Au nanoshells by vancomycin treatment and then with the exposure of two-photon femtosecond Ti:sapphire nonlinear laser.

FIG. 13-j2 shows images of MRSA coated with Au nanoshells by vancomycin treatment and then with the exposure of two-photon femtosecond Ti:sapphire nonlinear laser.

FIG. 13-k1 shows the CFU viability test of FIGS. 13-a1, 13-f1, 13-i1 and 13-j1 quantified.

FIG. 13-k2 shows the CFU viability test of FIGS. 13-a2, 13-f2, 13-i2 and 13-j2 quantified.

FIG. 14-a1 shows images of *Staphylococcus aureus* after they had been exposed to femtosecond Ti:sapphire nonlinear laser with the power of 70 mW.

FIG. 14-a2 shows images of *Staphylococcus aureus* after they had been exposed to femtosecond Ti:sapphire nonlinear laser with the power of 80 mW.

FIG. 14-a3 shows images of *Staphylococcus aureus* after they had been exposed to femtosecond Ti:sapphire nonlinear laser with the power of 90 mW.

FIG. 14-b1 shows images of *Staphylococcus aureus* coated with Au nanoshells after they had been exposed to femtosecond Ti:sapphire nonlinear laser with the power of 70 mW.

FIG. 14-b2 shows images of *Staphylococcus aureus* coated with Au nanoshells after they had been exposed to femtosecond Ti:sapphire nonlinear laser with the power of 80 mW.

FIG. 14-b3 shows images of *Staphylococcus aureus* coated with Au nanoshells after they had been exposed to femtosecond Ti:sapphire nonlinear laser with the power of 90 mW.

FIG. 15-a1 shows images of MRSA after they had been exposed to femtosecond Ti:sapphire nonlinear laser with the power of 70 mW.

FIG. 15-a2 shows images of MRSA after they had been exposed to femtosecond Ti:sapphire nonlinear laser with the power of 80 mW.

FIG. 15-a3 shows images of MRSA after they had been exposed to femtosecond Ti:sapphire nonlinear laser with the power of 90 mW.

FIG. 15-b1 shows images of MRSA coated with Au nanoshells after they had been exposed to femtosecond Ti:sapphire nonlinear laser with the power of 70 mW.

FIG. 15-b2 shows images of MRSA coated with Au nanoshells after they had been exposed to femtosecond Ti:sapphire nonlinear laser with the power of 80 mW.

FIG. 15-b3 shows images of MRSA coated with Au nanoshells after they had been exposed to femtosecond Ti:sapphire nonlinear laser with the power of 90 mW.

FIG. 16-*a* shows the photoluminescence spectra of *E. coli* (BL21) coated with Au nanoshells which were exposed to femtosecond Ti:sapphire nonlinear laser. BL21 and *Bacillus subtilis* nanomaterials were irradiated, respectively (indicated by a blue color). On the other hand, spectra indicated by a red color meant that bacteria alone had undergone photothermolysis after the same laser exposure.

FIG. 16-*b* shows the photoluminescence spectra of *Bacillus subtilis* coated with Au nanoshells which were exposed to femtosecond Ti:sapphire nonlinear laser. BL21 and *Bacillus subtilis* nanomaterials were irradiated, respectively (indicated by a blue color). On the other hand, spectra indicated by a red color meant that bacteria alone had undergone photothermolysis after the same laser exposure.

FIG. 16-*c* shows the photoluminescence spectra of MRSA coated with Au nanoshells which were exposed to femtosecond Ti:sapphire nonlinear laser. BL21 and *Bacillus subtilis* nanomaterials were irradiated, respectively (indicated by a blue color). On the other hand, spectra indicated by a red color meant that bacteria alone had undergone photothermolysis after the same laser exposure.

FIG. 17-a1 shows a wound made on mouse's ear and then inoculated bacteria (indicated by the yellow arrows).

FIG. 17-a2 shows a wound made on mouse's ear and then inoculated *Staphylococcus aureus* and showing reflection signals as seen by the predominance of red fluorescence indicating the bacterial nanomaterials.

FIG. 17-a3 shows the photoluminescence spectra after dropping Au NPs producing solution on the wound to incubate, with the ear-wounded live mice irradiated with femto second Ti:sapphire nonlinear laser. The photoluminescence generated by *Staphylococcus aureus* coated with Au nanoshells was as indicated by the prevalence of a green fluorescence.

FIG. 17-b1 shows a wound made on mouse's ear and then inoculated with bacteria (indicated by the yellow arrows).

FIG. 17-b2 shows a wound made on mouse's ear and then inoculated with MRSA and showing reflection signals as seen by the predominance of red fluorescence indicating the bacterial nanomaterials.

FIG. 17-b3 shows the photoluminescence spectrum after dropping Au NPs producing solution on the wound to incubate, with the ear-wounded live mice irradiated with femto second Ti:sapphire nonlinear laser. The photoluminescence generated by MRSA coated with Au nanoshells was as indicated by the prevalence of a green fluorescence.

DESCRIPTION OF THE PREFERRED EMBODIMENTS

Figure 1:
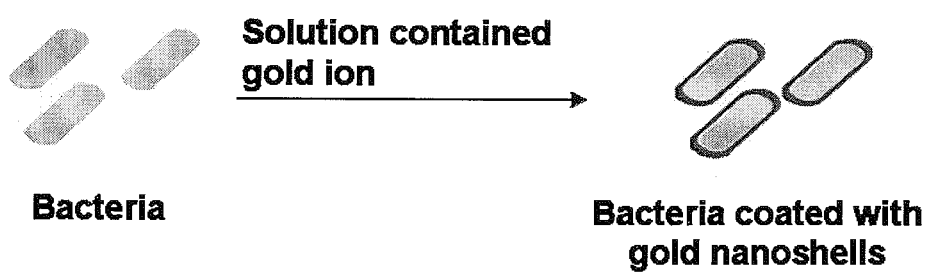
FIG. 1 shows a diagram of self-assembling bacteria coated with Au nanoshells.
Figure 2:
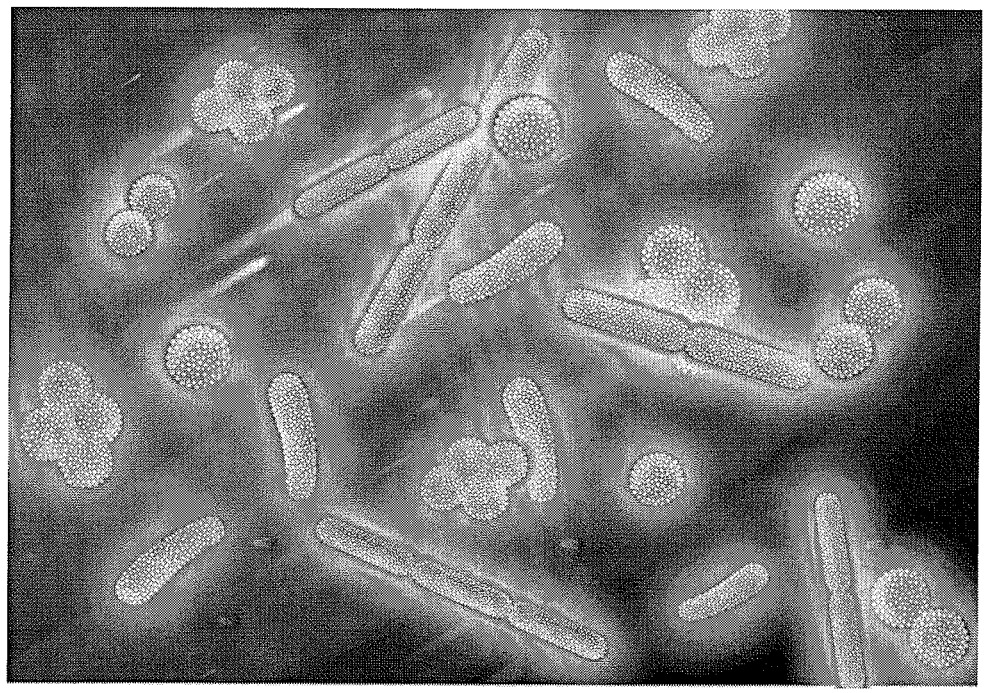
FIG. 2 shows a diagram of this patent.

The invention utilized the bacteria coated with Au nano shells to produce photothermolytic effect and generate photoluminescence which is a novel way to kill bacteria and track bacteria. In this invention, the Gram-negative bacteria of *E. coli* BL21, and Gram-positive bacteria of *Bacillus subtilis*, MRSA were utilized as our experimental templates to prepare Au nanoshells. It was that the Au ions were reduced from the solution contained Au ion to form Au NPs and then deposited them on the bacterial surface which was crystalline surface layer (S-layer). Suggest that the aldehyde with hydroxyl group of identical proteins or glycoproteins, and the ionized groups of amino acid residues on S-layer could serve as sites for $Au^{3+}$ ion binding, and that the aldehyde groups from the reducing sugars act as electron donors that reduce $Au^{3+}$ ion to $Au^0$ atom. We used several tools to characterize this nanomaterial. (1) The bare strain of BL21, *Bacillus subtilis* and MRSA respectively (FIGS. 3*a*, 3*d* and 3*g*) to incubate with the solution contained Au ion resulted in the shell formation of Au nanomaterials with a state of aggregation on the bacterial surface were imaged (FIGS. 3*b*, 3*e* and 3*h*). Bacteria are mainly composed of identical proteins or glycoproteins on the S-layers, and (2) IR spectrum can provide another way to characterize the situation of Au ion interacting with those molecules on S-layer which is suggested the principal site of this biological binding. According to the transmission percentage, bare BL21 showed the strong band of O—H coupled with C—O, the O—C=C asymmetric stretching and the symmetric carboxyl ion $C(=O)_2$ stretching of amino acid side chain, respectively (FIG. 4*a*). After the Au nanoshells formation, the bands mentioned above were disappeared or shifted to longer wavelength. Other different bacteria, *Bacillus subtilis* and MRSA, were studied and exhibited the same results (FIG. 4*b-c*). (3) XRD and EDX measurements were also used to investigate the properties of Au nanomaterials and confirm the composition of the Au nanoshells, determined the Au NP were crystalline Au, by these methods (FIG. 5). (4) Besides, STEM was able to be utilized to determine the form of Au material nanoshells. For BL21, FIG. 3*c* respectively represents that it showed very clear and dense self-aggregation layers constructed like the shape of nanoshell were coated on bacterial surface, so do *Bacillus subtilis* and MRSA (FIGS. 3*f* and 3*i*). After these characterizations, we can confirm that Au nanoshells were successfully self-assembling and self-synthesizing on the surfaces of these three different bacteria, including Gram-negative, Gram-positive bacteria and different shapes. According to these results, we can confirm that the Au nanoshells were successfully self-assembled on the S-layer of bacterial surface.

FIG. 6*a* shows the Au ion binding and Au NPs formation efficiency on-the S-layer of bacterial surface as a function of incubation time. The binding rate in percentage of three bacteria showed a similar tendency and rapidly increased and increased the particle density and thickness of nanoshells with incubation time. Besides, UV/Vis spectra of bacteria coated with Au nanoshells were monitored for the evolution of Au NPs (FIG. 7). As the incubation time increased, the Au nanoshells would get thickening and cause the absorptions to raise and move to the NIR region. This is one more way to demonstrate the successful coating of Au NPs on the surface of bacteria. With these characterizations, the results prove that Au nanoshells were succeeded and well-coated on different kinds of bacterial surface. On the other hand, the THG is highly sensitive to the interface between two different materials (with different refractive indexes or $\chi^{(3)}$) and was utilized to investigate the Au nanoshells under high spatial resolution by a femtosecond Cr: forsterite nonlinear laser microscopy; therefore, the morphology of chosen BL21 coated with Au nanoshells can be sequentially revealed by using THG signals. THG was used to investigate Au nanoshells coated on the BL21 surface under high spatial resolution. The bacteria remained alive under the Au nanoshell coating, even after the incubation in the solutions had been extended to several weeks, respectively (FIG. 6*b*). The viability of bacteria coated with Au nanoshells was also able to be examined using a LIVE/DEAD kit to stain bacteria according to the manufacturer's instructions. Under the same condition, most of the self-assembling BL21 still showed no damage as seen by the predominance of green fluorescence (SYTO 9) indicating live bacteria, whereas dead bacteria were indicated by the prevalence of red fluorescence (propidium iodide) (FIG. 6*c*). FIG. 6*d* shows bacteria seemed to be undergoing the segregation of binary fission.

Due to Au with the high efficiency to convert absorbed radiation into heat for serving as photothermolytic agents, the temperature elevation test of these nanomaterials should be conducted first. Au nanoshells coated on the bacterial surface were exposed to an 808 nm CW diode linear laser as a function of exposure time to examine the temperature elevation (FIG. 8). Results show bacteria coated with Au nanoshells displayed a photothermolytic heating ability and could act as promising photothermolytic mediators.

Figure 9:
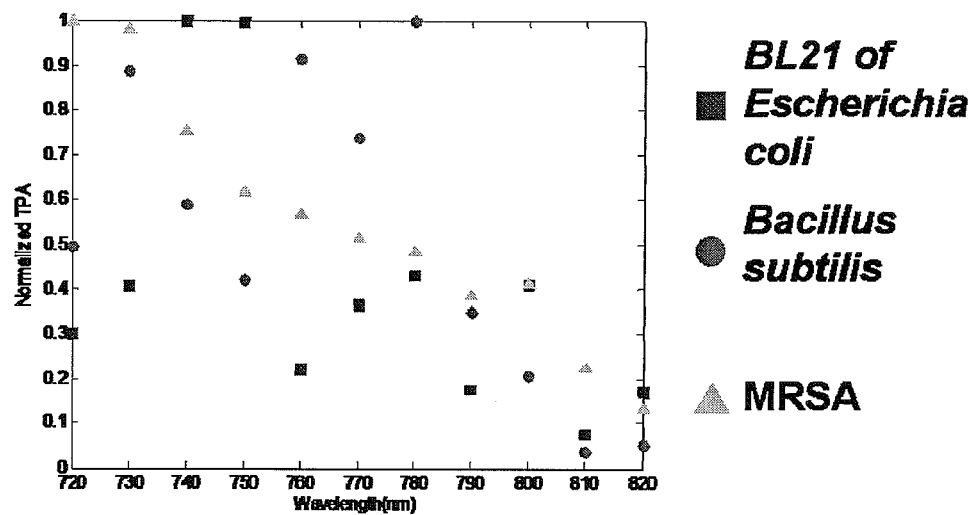
FIG. 9 shows the relative TPA spectrum of the bacteria coated with Au nanoshells as a function of excitation wavelength and monitored by femtosecond Ti:sapphire nonlinear laser.

On the other hand, we would like to understand whether these bacterial nanomaterials could be photothermolytic mediators by multiphoton laser exposure as well except for one-photon excitation. However, nonlinear optics effect is highly related to TPA, which the corresponding excitation occurs about twice the wavelength in the IR region at which one-photon excitation occurs. Au nanoshells coated on the bacterial surface were exposed to a nonlinear pulse two-photon femtosecond laser to examine the TPA (FIG. 9). However, results of the spectra for one- and multiphoton were effectively utilized due to low scattering and energy absorption in NIR region and applied in following experiments.

To make the bacteria coated with Au nanoshells a functional photothermolytic bacterial nanomaterial, we analyzed its potential use in photothermolytic antimicrobial therapy. Bacterial nanomaterials irradiated at 808 nm using a CW-NIR linear laser, after which, the bacteria were stained using the cell LIVE/DEAD viability kit. Bacterial nanomaterials that had not been exposed to the laser showed almost no damage as seen by the predominance of green fluorescence indicating live bacteria (FIG. 10*a*). However, the number of dead bacteria discernibly increased in the group of bacteria coated with Au nanoshells and irradiated with the laser, as indicated by the prevalence of red fluorescence (FIG. 10*b*). To better understand the efficacy of photothermolytic antimicrobial ability in FIG. 10*a-b*, bacterial viabilities were quantified. Viability was significantly lower in the BL21 and *Bacillus subtilis* coated with Au nanoshells exposed to NIR laser than in those treated without irradiation (FIG. 10*c*). The CFU counting experiments showed similar results via the same treatment (FIG. 10*d*). Besides, due to obvious TPA of these bacterial nanomaterials in NIR, it might be possible to achieve bacterial photothermolysis with femtosecond Ti:sapphire nonlinear laser microscopy. FIGS. 10*e*, 11 show the bacterial nanomaterials emitted photoluminescence and it increased with time. But bacterial nanomaterials irradiated to CW-NIR linear laser showed almost no photoluminescence even after exposure (FIG. 12). On the other hand, the viability after femtosecond laser exposure was also needed to be estimated by using the same kit. Viability of BL21 and *Bacillus* subtilis nanomaterials fell to relative low with the same image observation process and quantification of viability method (FIG. 10f-g). Results presented the stronger photoluminescence was emitted, the more bacteria were killed.

To determine the photoluminescence emitted from dead bacteria coated with Au nanoshells, the different treatments of autoclave and ampicillin were conducted. Probably interactive sites of the reduced Au NPs on bacterial surface were destroyed via these processes, and sequentially there was no photoluminescence emitted from bacterial nanomaterials after femtosecond laser exposure (FIG. 10h-i). Alternatively, the CFU counting results also indicate bacteria were inactivated via these treatments (FIG. 10j). The Gram-negative or Gram-positive bacterial nanomaterials showed impressive photothermolytic efficacy by short-term and low-power laser exposure to reduce the viability of bacteria with laser irradiation, and then represented an excellent ability to emit photoluminescence after laser irradiation.

The continuous increase of MDR bacterial strains is a serious medical problem because of their ability to develop resistance to antibiotics that worked by permeating inside bacterial cell wall and interfering with essential their processes through different pathways, such as mutation, conjugation, transduction and transformation. Because of the growing resistance of MRSA to conventional antimicrobial agents, it is desirable to develop alternative approaches to eliminate MDR bacterial strains. MRSA, antibiotic-resistant-Gram-positive MDR bacteria, are resistant to many antibiotics and are often associated with diseases.

We were curious about whether MRSA nanomaterials would showed the prominent photothermolytic ability. The strain of *Staphylococcus aureus* coated with Au nanoshells was chose as control to compare with the efficacy of MRSA nanomaterials. There is no deactivating effect occurred with no laser exposure (FIG. 13a). To test the ability of elimination to *Staphylococcus aureus* and MRSA coated with Au nanoshells, the vancomycin was pre-treated to these nanomaterials without exposure and then observed. We found the strong MDR ability to vancomycin on MRSA was indeed shown than that of *Staphylococcus aureus* (FIG. 13b), as indicated by the prevalence of green and red fluorescence for the live and dead bacteria, respectively. The results also confirmed to the characteristic of MRSA that was resistant to conventional and low-dosage antibiotic treatment. For CW-NIR linear laser exposure, both of these nanomaterials exhibited unexpectedly photothermolytic ability, and in particular MRSA nanomaterials (FIG. 13e). After the same image observation process and quantification method described above, MRSA were killed and viability was down to very low extent (FIG. 13d). The CFU counting shows similar results as that of quantified viability analysis (FIG. 13e).

Figures 1, 15B:
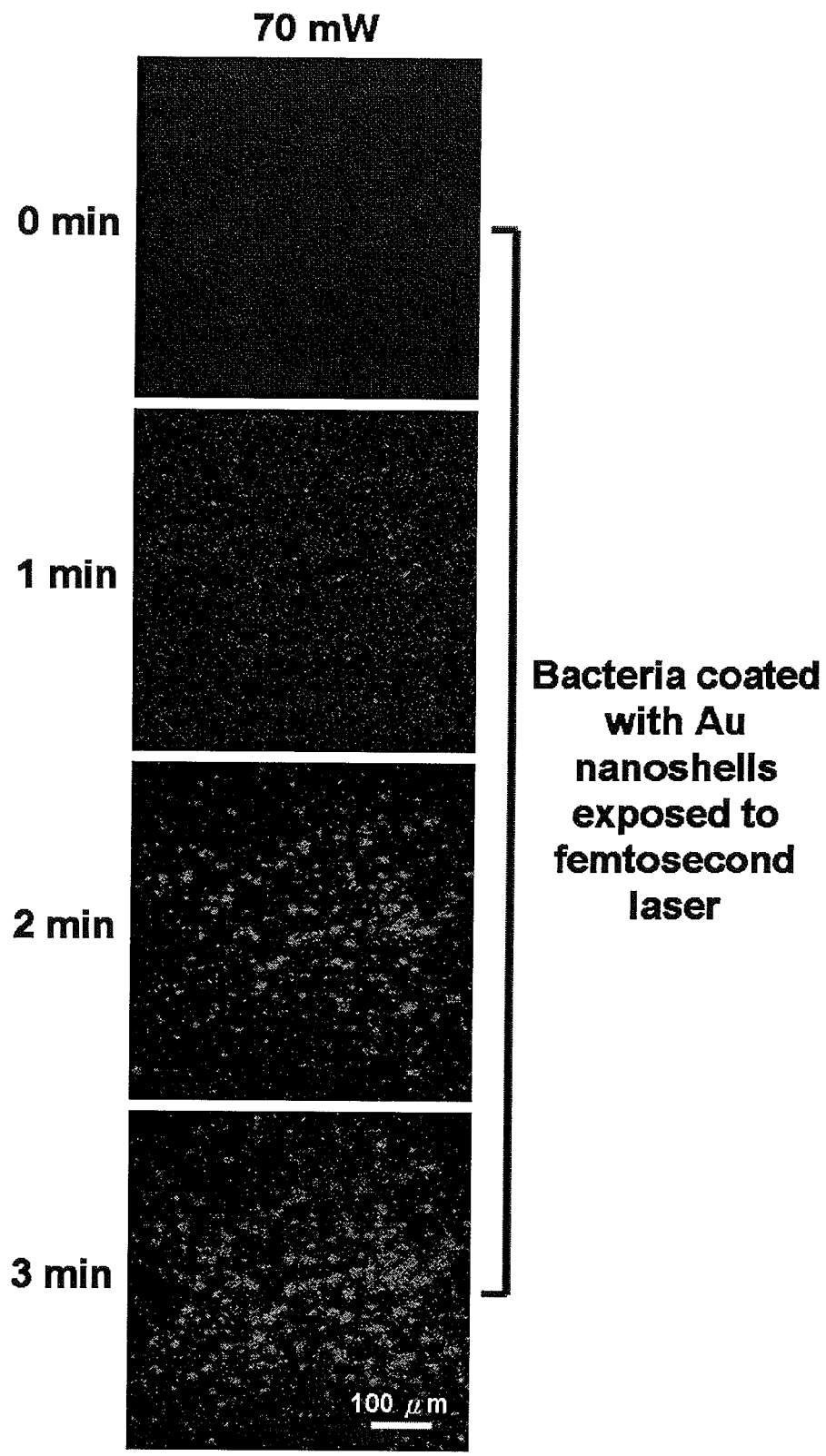
Figures 2, 15B:
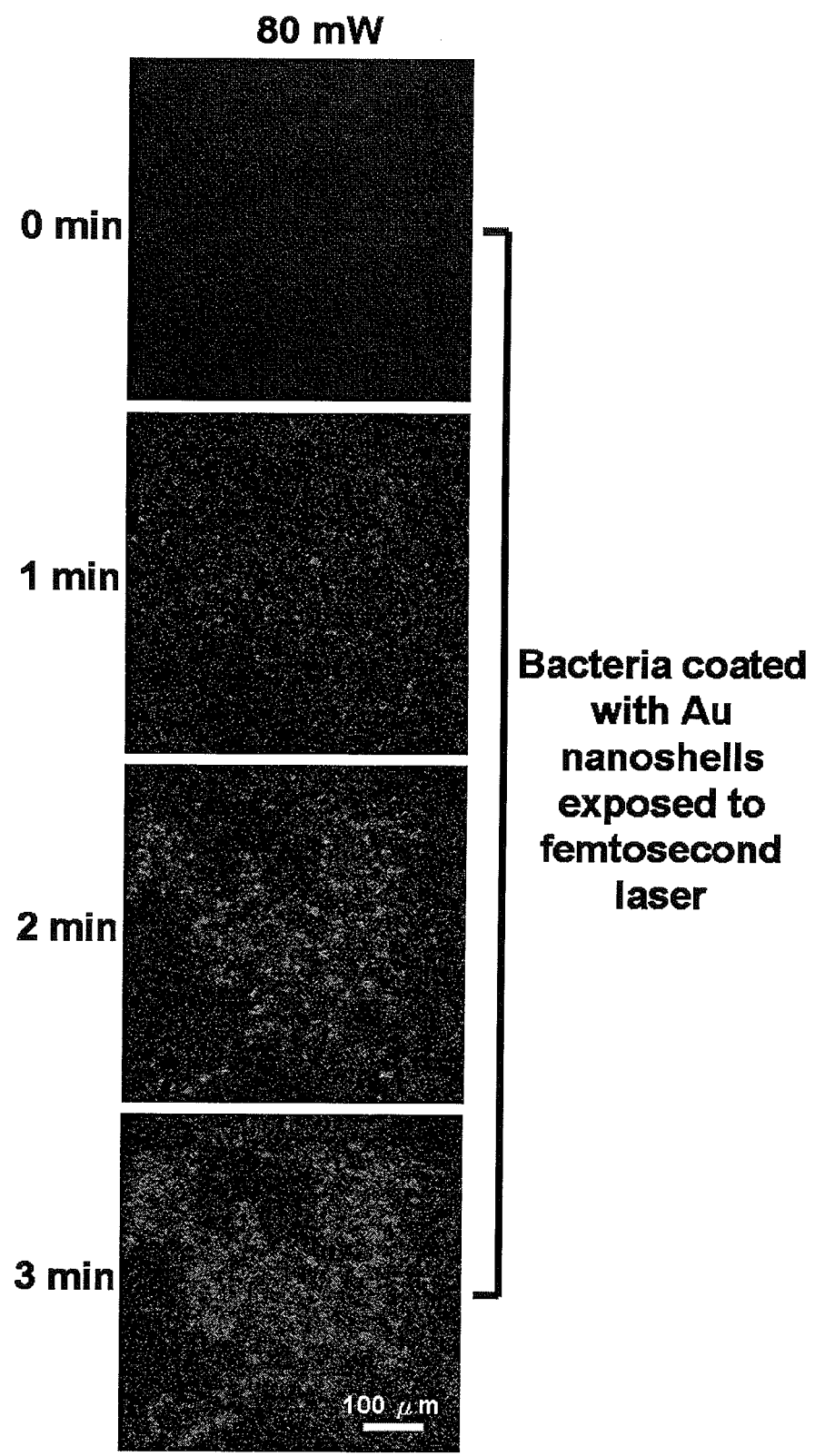
Figures 3, 15B:
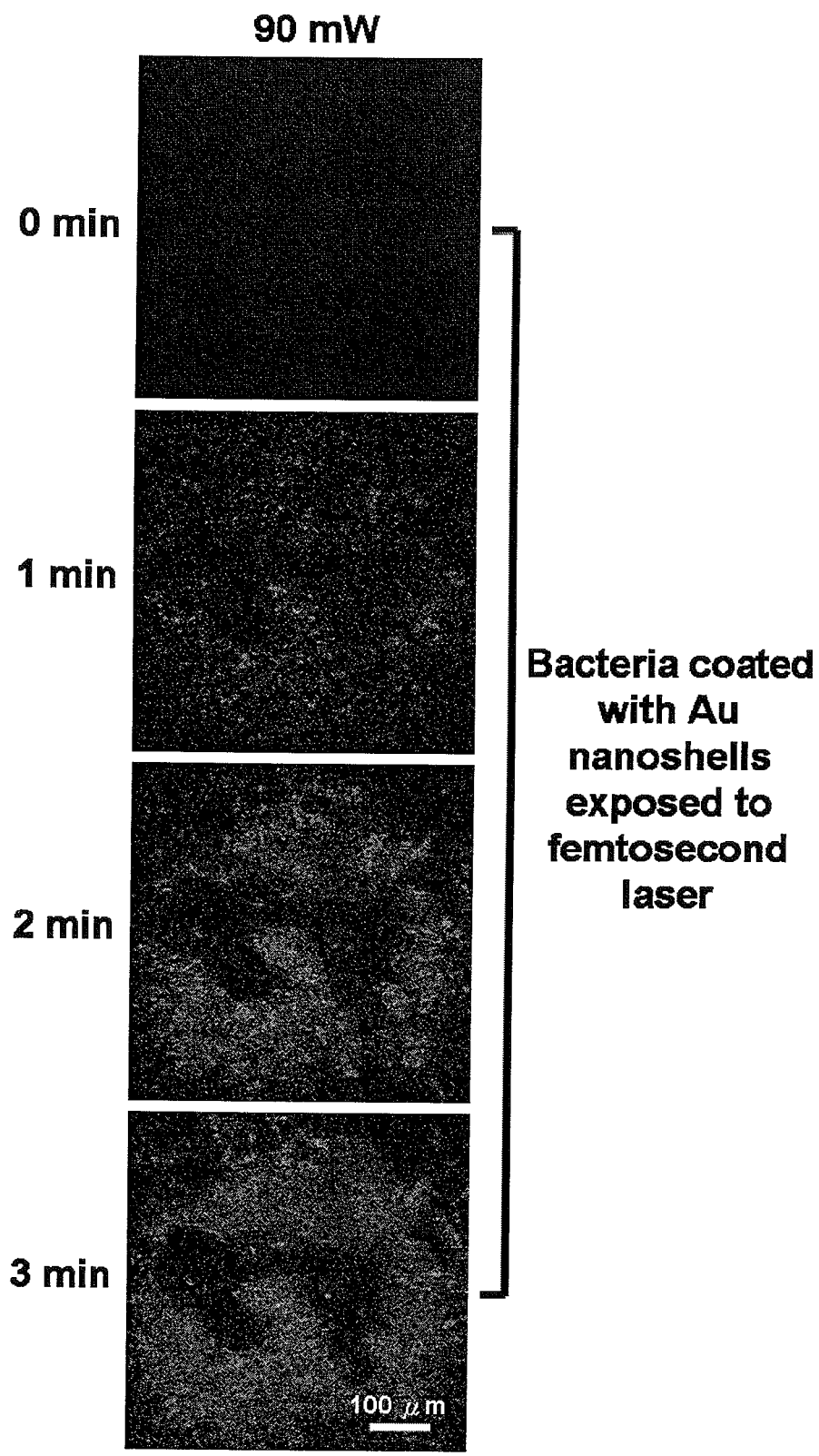
FIG. 3-$a$ shows images of E. coli (BL21) without Au nanoshells characterized by transmission electron microscopy (TEM).

On the other hand, after femtosecond nonlinear laser exposure, both of *Staphylococcus aureus* and MRSA coated with Au nanoshells emitted the same photoluminescence as BL21 and *Bacillus subtilis* nanomaterials (FIG. 13f, FIGS. 14 and 15). The viability after femtosecond nonlinear laser exposure was quantified with the LIVE/DEAD kit, and viability of *Staphylococcus aureus* and MRSA nanomaterials fell to very low extent, which were similar results to that of CW-NIR linear laser treatment, after laser exposure (FIG. 13g-h). No photoluminescence was produced via treatments of autoclave and vancomycin, and sequentially showed almost no bacteria alive via CFU counting test (FIG. 13i-k).

Due to these results, bacteria coated with Au nanoshells via different lasers with short-term and low-power irradiation were able to exhibit powerful photothermolytic ability to eliminate bacteria possessing different properties of strains, shapes and drug-resistance. If irradiating for longer exposure time, the bacterial nanomaterials must eliminate 100% bacteria and no matter what bacteria were conducted and examined. Besides, the photoluminescence generated from the dead bacteria coated with Au nanomaterials after laser irradiation was definitely able to serve as contrast agent or indicator to determine viability of bacteria. The photoluminescence similar to two-photon luminescence in this invention which was able to sustain femtosecond laser exposure, keep luminescence emitted and prevent from photobleaching was still generated. Furthermore, results showed as soon as laser irradiation, the bacterial nanomaterials emitted the photoluminescence immediately and then the more bacteria dead, the stronger emission to a saturated intensity as a function of irradiation time. In other words, the bacterial nanomaterials had the capability to emit photoluminescence with only little femtosecond laser energy. Due to the reasons mentioned above and good TPA in NIR region of these bacterial nanomaterials, we examined the TPL spectra of BL21, *Bacillus subtilis* and MRSA coated with Au nanoshells to further understand the optical properties of these nanomaterials. FIG. 16 shows the spectra of bacterial nanomaterials, as seen by blue color indicating after photodestruction, whereas red color meant bacterial alone after exposure. Not only photoluminescence was obviously taken place from these bacterial nanomaterials, but it was a very easy way to distinguish live bacteria from dead ones by the spectra after laser exposure.

By integration of the advantages of bacterial nanomaterials, multimodal contrast probes with non-toxic to bacteria, impressive photothermolytic efficacy, excellent photoluminescence emission capability had great potential in therapy and diagnosis. To apply in therapeutic biomedical application, in vivo test was necessary to conduct and MRSA coated with nanomaterials in particular. A wound was made on mouse's ear and inoculated with *Staphylococcus aureus* and MRSA to proliferate and infect mice, respectively; then, adding the solution contained Au ion on wound to incubate and produce Au nanoshells and exposed to femtosecond nonlinear laser (FIG. 17). After exposure, the green light (photoluminescence) generated and emitted from bacterial nanomaterials showed for dead bacteria, whereas the prevalence of red fluorescence indicated reflection signal from nanomaterials, and bubble formation due to heat production. According to red and green light distributions, it can make sure that the bacteria were almost deactivated and eliminated. Results show that Au nanoshells were able to be coated on bacterial surface via this way, and this tool exhibited outstandingly antimicrobial efficacy in *Staphylococcus aureus* as well as in MRSA resulted in being less able to develop resistance. Results showed this contrast agent is therefore expected to be applicable in clinical therapy and diagnosis in the future.

The invention claimed is:

1. A method for tracing and killing bacteria by making a nanomaterial of the bacteria that are coated with self-assembly Au nanoshells and drawing support from laser-generated photothermolysis and luminescence, the method being characterized in comprising the following steps:

selecting the bacteria as a biological template;

mixing the bacteria with a solution containing Au ions for culture, wherein since surfaces of the bacteria each has an S layer composed of glycoproteins, and carboxyl groups in the glycoproteins in the S layer and ionized carboxyl groups of amino acid residues peptide chains act as sites for acting with the Au ions, hydrolysates of the glycoproteins such as hemiacetal hydroxyl groups of reducing sugar or free-state aldehyde groups act as electron donors for oxidation-reduction reaction, which reduces the Au ions into Au nanoparticles that deposit on the surfaces of the bacteria, so as to form the nanomaterial of the bacteria coated with the Au nanoshells; and exposing the nanomaterial to linear and non-linear laser, so as to generate heat that effectively kills the bacteria.

2. The method of claim 1, being characterized in that: the solution containing the Au ion comprises: a tetrachloroauric acid solution, a complex ion solution containing gold, a trichloropyridinegold solution or a potassium tetrachloroaurate solution.

3. The method of claim 1, being characterized in that: in the step of exposing the nanomaterial to the linear and non-linear laser, the nanomaterial is exposed to the non-linear laser so as to produce photothermolysis on the bacteria coated with the Au nanoshells.

4. The method of claim 3, being characterized in that: the nanomaterial after exposed to the non-linear laser possesses an optical property of generating the luminescence, so as to continuously luminesce without photobleaching, and as such exposure prolongs, heat-generating effect on the nanomaterial becomes increasingly obvious so as to kill more of the bacteria and generate the luminescence stronger, wherein the luminescence acts as an indicator of survival of the bacteria.

5. The method of claim 1, being characterized in that: in the step of exposing the nanomaterial to the linear and non-linear laser, where the nanomaterial is exposed to the linear laser, the nanomaterial absorbs the laser well in a near-infrared wavelength range between 700 nanometers and 1400 nanometers, so that when exposed to the continuous linear laser providing excitation light having a wavelength of 808 nanometers, the nanomaterial is effectively heated to kill the bacteria with effects of photolysis.

6. The method of claim 1, being characterized in that: in the step of exposing the nanomaterial to the linear and non-linear laser, where the nanomaterial is exposed to the non-linear laser, the nanomaterial absorbs the laser well in a near-infrared wavelength range between 700 nanometers and 1400 nanometers, so that when exposed to the pulsed non-linear femtosecond laser providing excitation light having a wavelength of a wavelength between 720 and 820 nanometers, the nanomaterial is effectively heated to kill the bacteria with effects of photolysis.

7. The method of claim 1, being characterized in that: the luminescence generated when the bacteria coated with the Au nanoshells in the nanomaterial are killed by the heat acts as an indicator for tracking and identifying survival, dynamics and locations of the bacteria in a wound.

8. The method of claim 1, being characterized in that: the bacteria are *Escherichia coli, Bacillus subtilis*, non-methicillin-resistant *Staphylococcus aureus* or methicillin-resistant *Staphylococcus aureus*.

9. The method of claim 1, being characterized in that: a mixture of the solution containing the Au ions and the bacteria is cultured in vivo for a period of time so as to generate the bacteria coated with the Au nanoshells, and when exposed to the non-linear laser, generates photothermolysis and luminescence in vivo, so as to kill the bacteria and trace survival of the bacteria.

* * * * *